United States Patent [19]

Takeda et al.

[11] Patent Number: 4,970,307

[45] Date of Patent: Nov. 13, 1990

[54] PROCESS FOR FORMATION OF BASE AND LIGHT-SENSITIVE MATERIAL

[75] Inventors: Keiji Takeda; Jiro Tsukahara; Kozo Sato, all of Kanagawa, Japan

[73] Assignee: Fuji Photo Film Co., Ltd., Kanagawa, Japan

[21] Appl. No.: 84,789

[22] Filed: Aug. 13, 1987

[30] Foreign Application Priority Data

| | | | |
|---|---|---|---|
| Aug. 13, 1986 | [JP] | Japan | 61-191000 |
| Aug. 22, 1986 | [JP] | Japan | 61-197964 |
| Oct. 14, 1986 | [JP] | Japan | 61-243555 |

[51] Int. Cl.[5] ...................... C07C 69/52; C07C 69/76; C07D 213/55; G03C 5/24

[52] U.S. Cl. .................................... 540/579; 544/242; 544/282; 544/330; 544/352; 544/358; 546/152; 546/186; 546/242; 546/244; 546/304; 546/311; 546/348; 548/199; 548/315; 548/323; 548/335; 548/347; 564/225; 564/240; 564/241; 564/391; 564/462; 564/463; 564/503; 564/506

[58] Field of Search ................ 540/579; 548/315, 347, 548/199, 323, 335; 544/330, 242, 358, 252, 352; 546/311, 244, 304, 242, 186, 348, 152; 564/246, 241, 225, 463, 462, 391, 503, 506

[56] References Cited

U.S. PATENT DOCUMENTS 4,560,763 12/1985 Sato .................................... 546/341

OTHER PUBLICATIONS

Toussaint, Tetrahedron, 40 3229 (1984).
Miyashita et al., Ag Bio. Chem. 45, 2521 (1981).
Chemical Abstracts 135390v, vol. 81, 1974 Entitled "Catalytic Decarboxylation of α-Acetylenic Acids", (Akopyan).
Chemical Abstracts 135032s, vol. 84, 1976 Entitled "Reaction of α-Acetylenic Acids in the Presence of Copper Salts," (Akopyan).
March Advanced Organic Chemistry, p. 562, (1985).
Akopyan, J. of Gen Chem. USSR, 44 (8)1804 (1974).

*Primary Examiner*—Robert Gerstl
*Attorney, Agent, or Firm*—Sughrue, Mion, Zinn, Macpeak & Seas

[57] ABSTRACT

A process for formation of a base from a base precursor, which comprises decomposing the base precursor in the presence of a catalyst. The base precursor has the following formula (I) or (II):

$$(R^1{-}C{\equiv}C{-}CO_2H)_x{\cdot}B \quad (I)$$

$$R^2({-}C{\equiv}C{-}CO_2H)_2{\cdot}B_y \quad (II)$$

wherein $R^1$ is a monovalent group selected from the group consisting of hydrogen, an alkyl group, a cycloalkyl group, an alkenyl group, an alkynyl group, an aryl group, a heterocyclic group, an aralkyl group, an acyl group, an alkoxycarbonyl group, carbamoyl, $-CO_2M$ (M is an alkali metal) and $-CO_2H.B$, each of which may have one or more substituent groups; $R^2$ is a divalent group selected from the group consisting of an alkylene group, an arylene group and a divalent heterocyclic group, each of which may have one or more substituent groups; B is an organic base; x is 1 when B is a monoacidic base, and x is 2 when B is a diacidic base; and y is 2 when B is a monoacidic base, and y is 1 when B is a diacidic base. The catalyst is selected from the group consisting of silver, a silver compound, copper and a copper compound. A light-sensitive material containing the base precursor and the catalyst is also disclosed.

4 Claims, 1 Drawing Sheet

PROCESS FOR FORMATION OF BASE AND LIGHT-SENSITIVE MATERIAL

BACKGROUND OF THE INVENTION

1. Field of the invention

The present invention relates to a process for formation of a base, and more particularly to a process for formation of a base from a base precursor which is substantially neutral during the storage. The invention also relates to a light-sensitive material comprising a light-sensitive layer containing silver halide, reducing agent and polymerizable compound provided on a support.

2. Description of prior art

Bases are reagents widely used in various reactions (e.g., hydrolysis, polymerization, coloration, redox reaction, and neutralization). A base component is incorporated into many products such as developing solutions in silver salt photographic processes, heat-developable light-sensitive materials, adhesives, detergents, etc.

However, the bases (particularly strong bases) have a problem with respect to stability in that they absorb carbon dioxide from air and are then inactivated. Further, the strong bases, which are highly reactive, have much difficulty in storing them in contact with other component. Furthermore, it is possible that the bases have harmful infuence on the human body, for example, they irritate the skin. Therefore, when bases are dealt with, it is necessary to pay attention to the toxicity and the skin irritation.

Accordingly, the products containing a base component have problems in the stability of the bases, the preservability of other component in contact with the base and the handling characteristics.

In order to eliminate the above-mentioned problems, it is proposed in Japanese Patent Provisional Publication No. 59(1984)-180537 (corresponding to U.S. Pat. No. 4,560,763 and European Patent Publication No. 0123937B1) to use a base precursor having the below-mentioned formula (I) or (II) in place of the conventional bases. As described in the patent publication, the base precursor having the formula (I) or (II) is very stable at ordinary temperatures. The base precursor can be rapidly decomposed to release a base, when it is heated at a certain temperature. Therefore, the base precursors are suitably used in a heat-developable light-sensitive material.

SUMMARY OF THE INVENTION

The present inventors have further studied a process for formation of a base from the base precursor having the following formula (I) or (II), which is very stable during the storage.

It is an object of the present invention to provide a process for formation of a base, which can more rapidly form a base from the base precursor having the formula (I) or (II).

There is provided by the present invention a process for formation of a base, which comprises decomposing the base precursor having the following formula (I) or (II):

$$(R^1—C\equiv C—CO_2H)_x.B \quad \text{(I)}$$

$$R^2(—C\equiv C—CO_2H)_2.B_y \quad \text{(II)}$$

wherein $R^1$ is a monovalent group selected from the group consisting of hydrogen, an alkyl group, a cycloalkyl group, an alkenyl group, an alkynyl group, an aryl group, a heterocyclic group, an aralkyl group, an acyl group, an alkoxycarbonyl group, carbamoyl, $—CO_2M$ (M is an alkali metal) and $—CO_2H.B$, each of which may have one or more substituent groups; $R^2$ is a divalent group selected from the group consisting of an alkylene group, an arylene group and a divalent heterocyclic group, each of which may have one or more substituent groups; B is an organic base; x is 1 when B is a monoacidic base, and x is 2 when B is a diacidic base; and y is 2 when B is a monoacidic base, and y is 1 when B is a diacidic base, in the presence of a catalyst selected from the group consisting of silver, a silver compound, copper and a copper compound.

The process for formation of a base of the present invention is characterized in that the base precursor having the formula (I) or (II) is decomposed in the presence of a catalyst selected from the group consisting of silver, a silver compound, copper and a copper compound.

The present inventors have found that silver, a silver compound, copper and a copper compound function as excellent catalysts for the decomposition reaction (base forming reaction) of the base precursor having the formula (I) or (II).

In the process for formation of a base of the invention, a base is formed by treating the base precursor with a catalyst selected from the group consisting of silver, a silver compound, copper and a copper compound. Therefore, the process of the present invention can easily and rapidly form a base from a combination of very stable materials (the catalyst and the base precursor).

A base can be further more rapidly formed when the base precursor is decomposed in the presence of the catalyst according to the present invention and under a heating condition as described in Japanese Patent Provisional Publication No. 59 (1984)-180537 (corresponding to U.S. Pat. No. 4,560,763 and European Patent Publication No. 0123937B1). Alternatively, the heating temperature in the heat treatment can be lowered when the process is carried out according to the present invention.

DETAILED DESCRIPTION OF THE INVENTION

Figure 1:
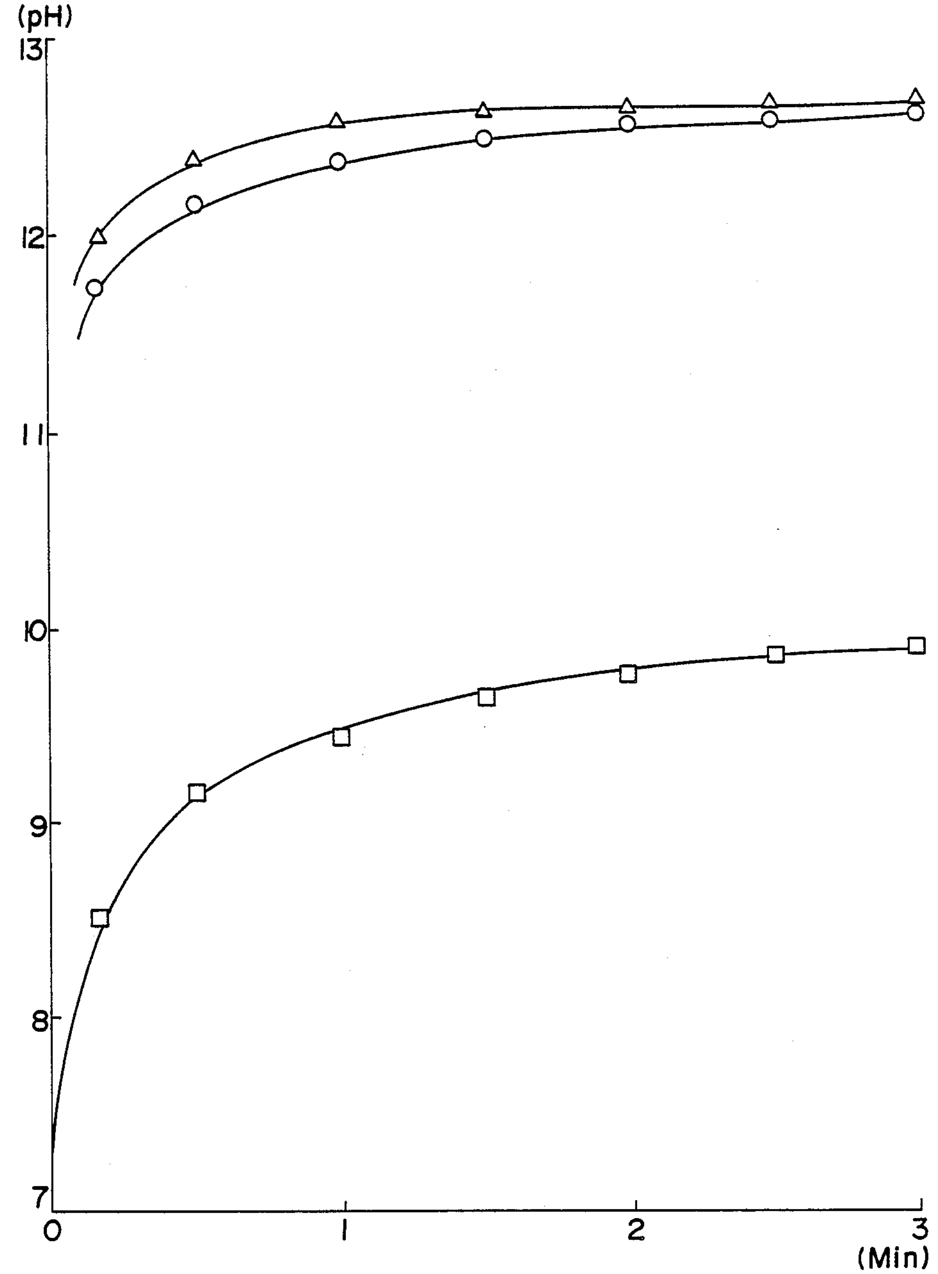
FIG. 1 is a graph illustrating pH change in a solution of a base precursor when the solution is heated at 80° C.

In the process of the present invention, the catalyst for the decomposition reaction of the base precursor is selected from the group consisting of silver, a silver compound, copper and a copper compound.

The silver compound and copper compound may be any of ionic compounds, covalent compounds and coordination compounds without particular limitation. The copper atom of the copper compound may be any of cuprous form and cupric form with respect to the valence. The silver compound and the copper compound may contain a ligand or water of crystallization. Further, the silver compound and the copper compound may be either soluble or insoluble in water or in an organic solvent. Thus, any of silver compounds and copper compounds can be used as the catalyst for the decomposition reaction of the base precursor.

Among these catalysts, copper and a copper compound are more preferred than silver and a silver compound, because copper and the copper compounds are superior in catalytic function and they are inexpensive. The silver compound and copper compound are preferably in the form of an oxide, a sulfide, a halide, a salt of a carboxylic acid and a substituted acetylide. A substituted cuprous acetylide is particularly preferred.

Preferred examples of the silver compound and the copper compound (salt or complex) have the following formula (III).

$$M'_m X_n L_l \qquad \text{(III)}$$

wherein M' is a cation derived from silver or copper; X is an anion; L is a ligand; m is 1 or 2; n is 0, 1 or 2; and l is an integer from 0 to 6.

Examples of the anion (X) in the formula (III) are described hereinafter.

$O^{2\ominus}$, (X-1)
$S^{2\ominus}$, (X-2)
$Cl^{\ominus}$, (X-3)
$Br^{\ominus}$, (X-4)
$I^{\ominus}$, (X-5)
$SO_4^{2\ominus}$, (X-6)
$NO_3^{\ominus}$, (X-7)
$PO_4^{3\ominus}$, (X-8)
$CN^{\ominus}$, (X-9)
$SCN^{\ominus}$, (X-10)
$CO_3^{2\ominus}$, (X-11)
$OH^{\ominus}$, (X-12)

(X-21)

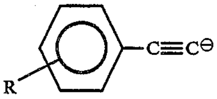

(X-22)

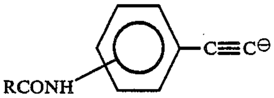

$R-CO_2^{\ominus}$ (X-23)

$R-SO_3^{\ominus}$ (X-24)

$R-C\equiv C^{\ominus}$ (X-25)

(X-26)

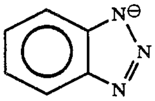

(X-27)

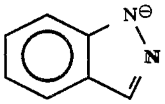

(X-28)

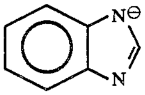

(X-29)

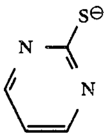

-continued (X-30)

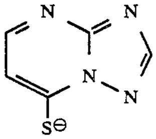

(X-31)

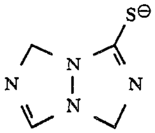

(X-32)

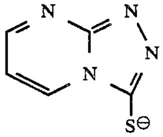

(X-33)

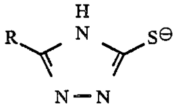

(X-34)

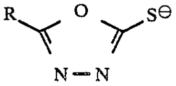

(X-35)

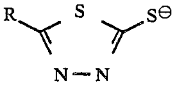

(X-36)

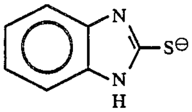

(X-37)

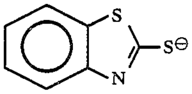

(X-38)

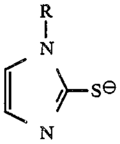

$R-N=N-N^{\ominus}-R$ (X-39)

(X-40)

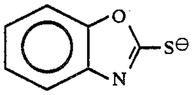

(X-41)

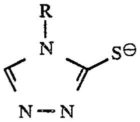

(X-42)

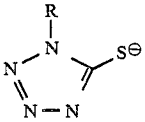

In the above formulae, R is a monovalent group selected from the group consisting of hydrogen, an alkyl group, a cycloalkyl group, an alkenyl group, an alkynyl group, an aryl group, an aralkyl group, a heterocyclic group and an acyl group. Each of the groups may have one or more substituent groups. Examples of the substituent group include a halogen atom, hydroxyl, an alkoxy group (preferably containing 1 to 20 carbon atoms), cyano, nitro, carbamoyl, sulfamoyl, an alkylsulfamoyl group (preferably containing 1 to 10 carbon atoms) and an acylamino group (preferably containing 1 to 10 carbon atoms).

Examples of the ligand (L) in the formula (III) include n-butylamine, ethylene diamine, triethanolamine, monoethanolamine, aniline, o-phenylene diamine, 2-pyridinecarboxylic acid, bipyridiine, salycylic acid, salicylaldehyde, ethylenediaminetetraacetic acid, nitrilotriacetic acid, oxalic acid, acetylacetone, benzoylacetone, thiourea, catechol, pyrogallol, dimethylglyoxime, salicylaldoxime, 8-hydroxyquinoline, o-phenanthroline, 1-(2-pyridylazo)-2-naphthol, glycine, alanine and serine.

Concrete examples of the catalyst which are preferably used in the invention are described below. (C-1) Metallic silver, (C-2) Metallic copper, (C-3) $Ag_2O$, (C-4) $Cu_2O$, (C-5) CuO, (C-6) $Ag_2S$, (C-7) $Cu_2S$, (C-8) CuS, (C-9) AgCl, (C-10) CuCl, (C-11) $CuCl_2$, (C-12) $CuCl_2.2H_2O$, (C-13) AgBr, (C-14) CuBr, (C-15) AgI, (C-16) CuI, (C-17) $AgNO_3$, (C-18) $Cu(NO_3)_2$, (C-19) $AgOCOCH_3$, (C-20) $CuOCOCH_3$, (C-21) AgCN, (C-22) CuCN, (C-23) $C_{21}H_{44}CO_2Ag$,

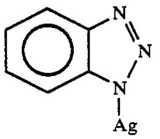
(C-24)

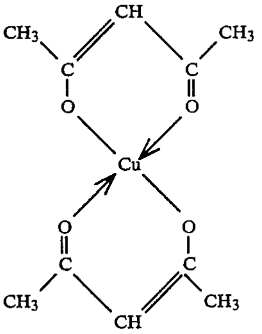
(C-25)

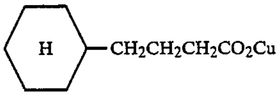
(C-26)

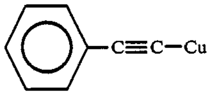
(C-27)

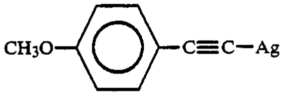
(C-28)

-continued

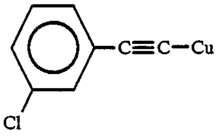
(C-29)

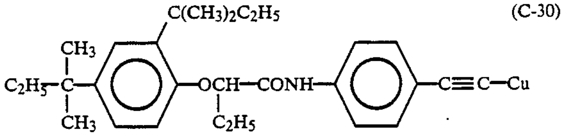
(C-30)

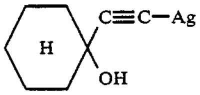
(C-31)

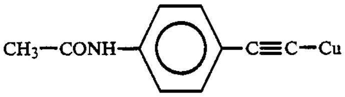
(C-32)

$C_8H_{17}—C≡C—Ag$ (C-33)

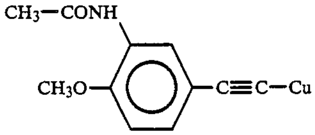
(C-34)

(Ethylenediaminetetraacetato) copper (II) complex (C-35)

$CuSO_4.5H_2O$ (C-36)

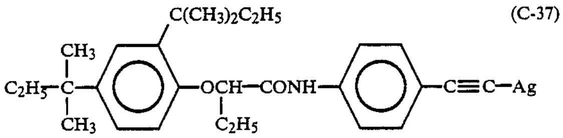
(C-37)

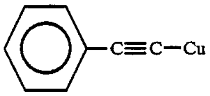
(C-38)

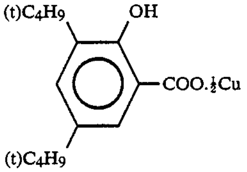
(C-39)

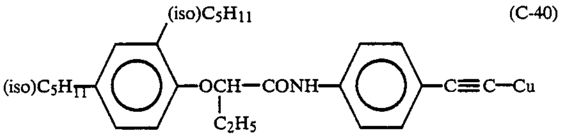
(C-40)

The catalyst can be used singly or in combination for the decomposition reaction of the base precursor. The catalyst is preferably used in an amount of 0.001 to 1 mole based on the amount of 1 mole of the following base precursor.

The base precursor having the following formula (I) or (II) is described below.

$$(R^1—C≡C—CO_2H)_x.B \quad (I)$$

$$R^2(-C\equiv C-CO_2H)_2.B_y \qquad (II)$$

The structural feature of the base precursor is that the acid moiety is a derivative of propiolic acid and a triple bond exists at the α-position of the carboxyl group. Therefore, the carboxyl group easily undergoes decarboxylation. However, the derivative of propiolic acid is very stable under storage conditions at ordinary temperatures in the absence of a catalyst for the decomposition reaction, and releases a base by decarboxylation only at an elevated temperature and/or in the presence of the catalyst.

In the formula (I), $R^1$ is a monovalent group selected from the group consisting of hydrogen, an alkyl group (preferably containing 1 to 5 carbon atoms), a cycloalkyl group (preferably containing 5 to 8 carbon atoms), an alkenyl group (preferably containing 2 to 5 carbon atoms), an alkynyl group (preferably containing 2 to 5 carbon atoms), an aryl group (e.g., phenyl, naphthyl, anthryl), a heterocyclic group (e.g., pyridyl, thienyl, thiazolyl, benzoxazolyl, benzothiazolyl), an aralkyl group (preferably containing 7 to 10 carbon atoms), an acyl group (preferably containing 2 to 12 carbon atoms), an alkoxycarbonyl group (preferably containing 2 to 9 carbon atoms), a carbamoyl group (preferably containing 2 to 9 carbon atoms), $-CO_2M$ (M is an alkali metal; e.g., $-CO_2Na$, $-CO_2K$) and $-CO_2H.B$ (B is an organic base), each of which may have one or more substituent groups.

In the formula (II), $R^2$ is a divalent group selected from the group consisting of an alkylene group, an arylene group (e.g., 1,3-phenylene, 1,4-phenylene, 1,5-naphthylene, 9,10-anthrylene) and a divalent heterocyclic group (e.g., thienylene), each of which may have one or more substituent groups.

It is preferred that $R^1$ and $R^2$ are properly electron attractive so that the base precursor having the formula (I) or (II) has a sufficient decomposition rate in the process of the present invention.

For this reason, $R^1$ preferably is a monovalent group selected from the group consisting of an alkenyl group, an alkynyl group, phenyl, naphthyl, anthryl, pyridyl, thienyl, benzoxazolyl, benzothiazolyl, an acyl group, an alkoxycarbonyl group, a carbamoyl group, $-CO_2M$ and $-CO_2H.B$, each of which may have one or more substituent groups.

Similarly, $R^2$ preferably is a divalent group selected from the group consisting of phenylene, naphthylene, anthrylene and thienylene, each of which may have one or more substituent groups.

$R^1$ more preferably is a monovalent group selected from the group consisting of phenyl, naphthyl, anthryl, pyridyl and thienyl, each of which may have one or more substituent groups, because these are easily available or can be simply synthesized.

In the formulas (I) and (II), B is an organic base. In the formula (I), x is 1 when B is a monoacidic base, and x is 2 when B is a diacidic base. In the formula (II) y is 2 when B is a monoacidic base, and y is 1 when B is a diacidic base.

There is no specific limitation with respect to the organic base (B). Therefore, the organic base can be determined according to the practical use of the base to be formed.

Examples of the base moiety (B) of the base precursor which can be used in the present invention are given below.

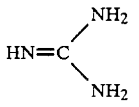
(B-1)

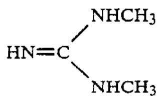
(B-2)

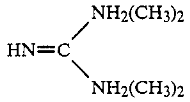
(B-3)

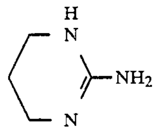
(B-4)

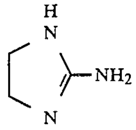
(B-5)

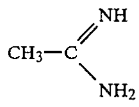
(B-6)

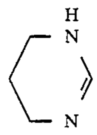
(B-7)

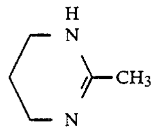
(B-8)

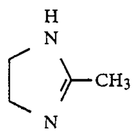
(B-9)

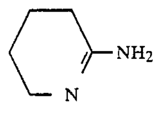
(B-10)

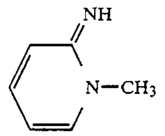
(B-11)

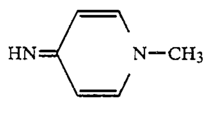
(B-12)

-continued
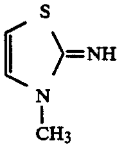
(B-13)
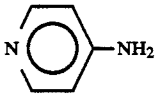
(B-14)
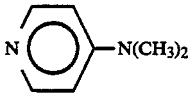
(B-15)
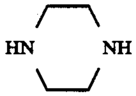
(B-16)
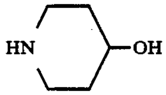
(B-17)
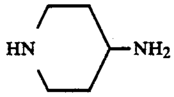
(B-18)
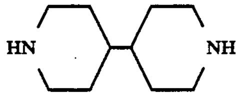
(B-19)
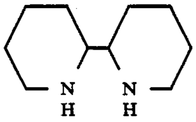
(B-20)
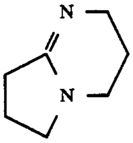
(B-21)
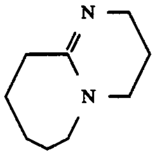
(B-22)
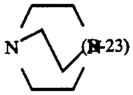
(B-23)
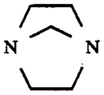
(B-24)
$C_6H_{13}NH_2$ (B-25)
-continued
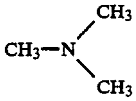
(B-26)
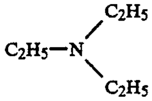
(B-27)
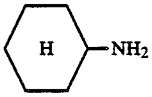
(B-28)
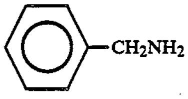
(B-29)
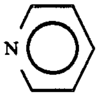
(B-30)
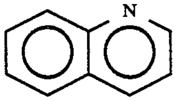
(B-31)
$H_2N-CH_2-CH_2-OH$ (B-32)
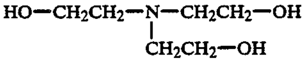
(B-33)
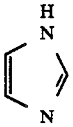
(B-34)
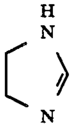
(B-35)
Examples of the preferred base precursor having the formula (I) or (II) which can be used in the present invention are described below.
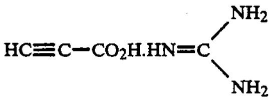
(P-1)
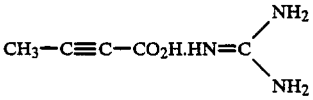
(P-2)
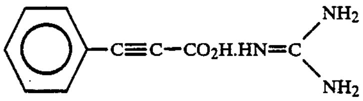
(P-3)

-continued
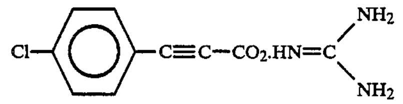
(P-4)
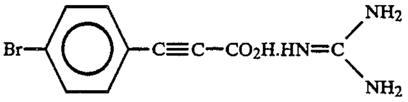
(P-5)
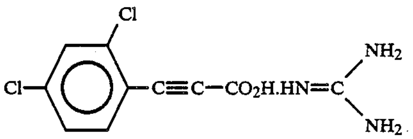
(P-6)
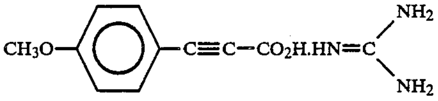
(P-7)
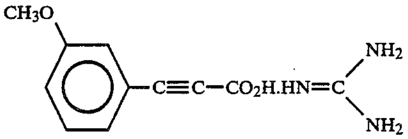
(P-8)
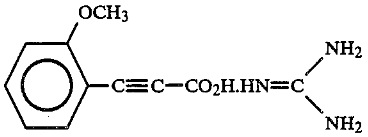
(P-9)
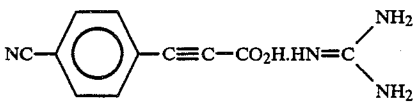
(P-10)
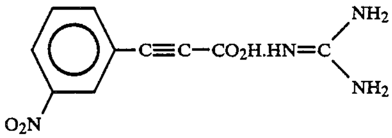
(P-11)
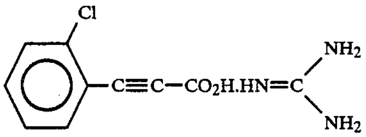
(P-12)
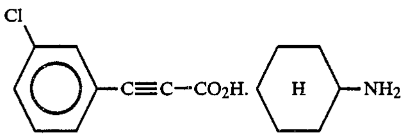
(P-13)
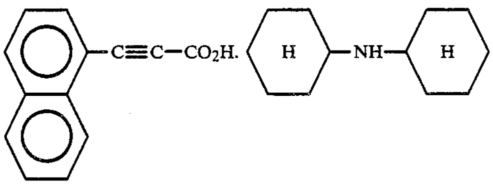
(P-14)
-continued
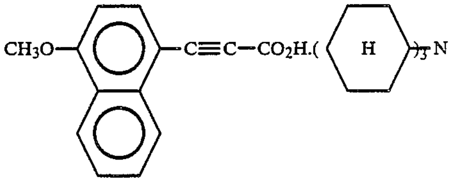
(P-15)
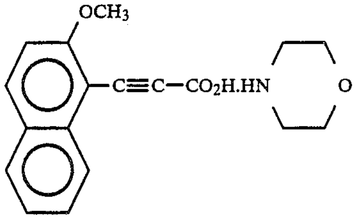
(P-16)
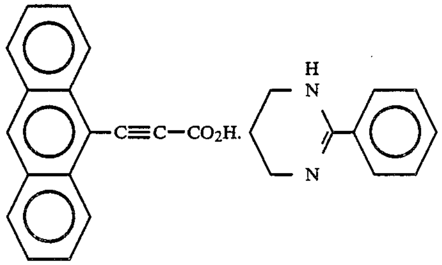
(P-17)
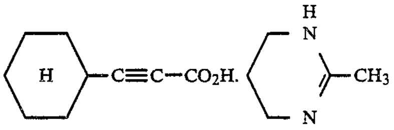
(P-18)
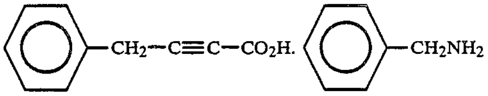
(P-19)
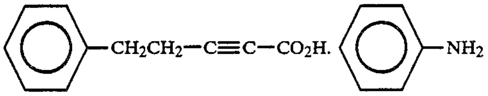
(P-20)
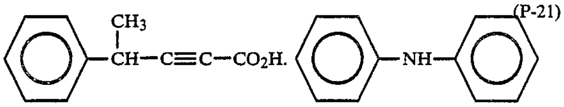
(P-21)
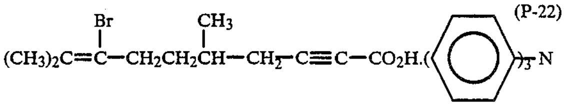
(P-22)
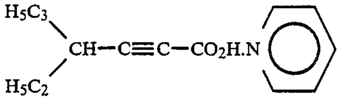
(P-23)
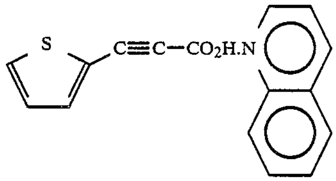
(P-24)

-continued
(P-25)
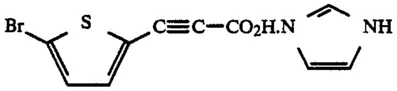
(P-26)
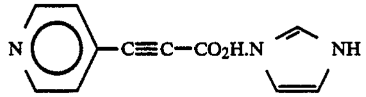
(P-27)
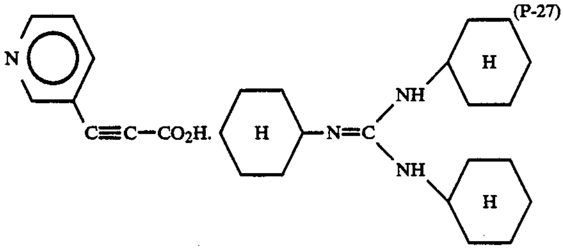
(P-28)
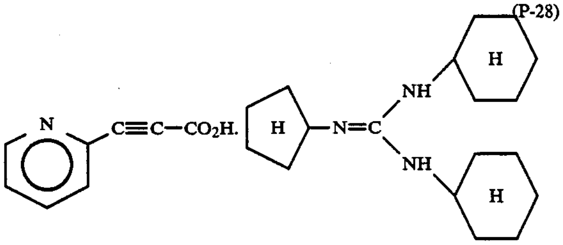
(P-29)
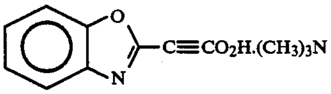
(P-30)
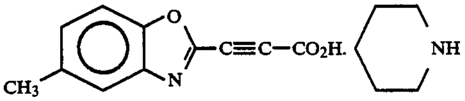
(P-31)
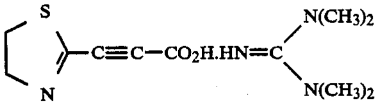
(P-32)
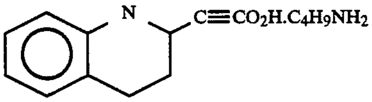
(P-33)
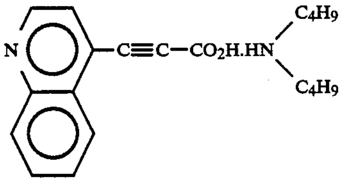
(P-34)
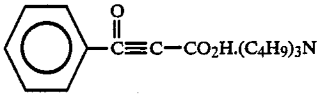
(P-35)
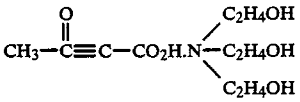
-continued
(P-36)
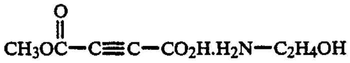
(P-37)
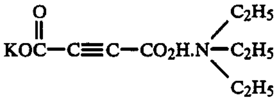
(P-38)
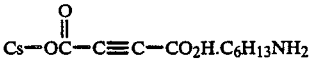
(P-39)
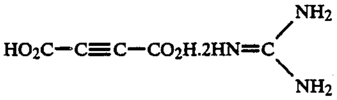
(P-40)
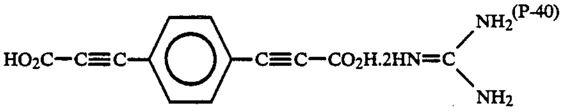
(P-41)
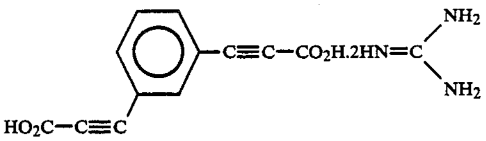
(P-42)
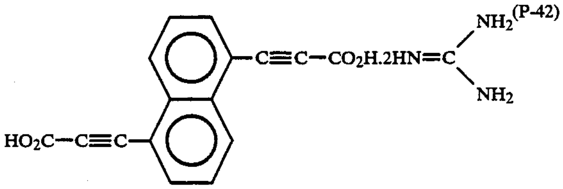
(P-43)
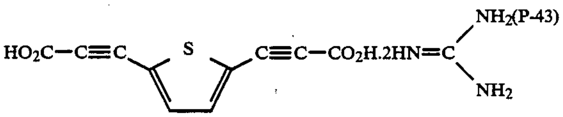
(P-44)
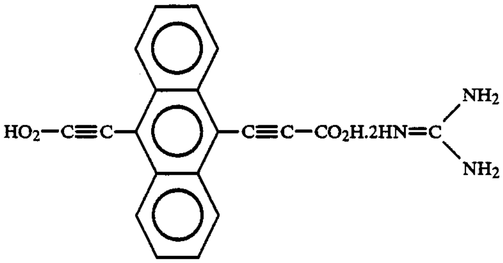
(P-45)
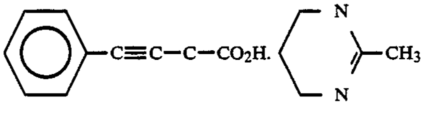
(P-46)
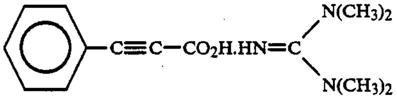

-continued (P-47)

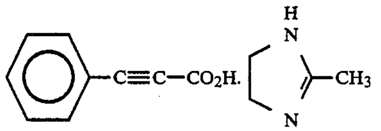

(P-48)

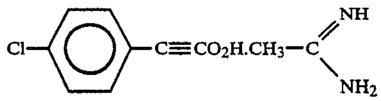

(P-49)

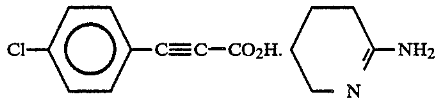

(P-50)

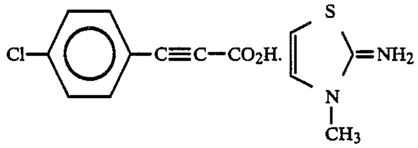

(P-51)

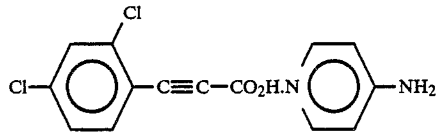

(P-52)

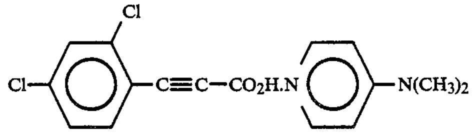

(P-53)

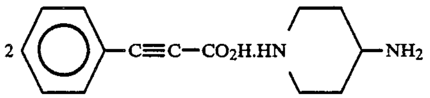

(P-54)

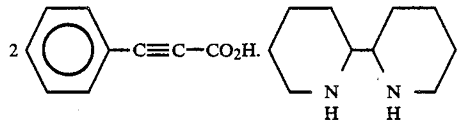

In the present invention, the base precursor is decomposed in the presence of a catalyst to form a base. The base precursor is preferably treated with the catalyst under a heating condition. The heating temperature is preferably not lower than 50° C.

The base forming process of the present invention can be effectively applied to various chemical reaction systems requiring a base component, such as image formation in a silver salt or diazotype photographic process, anionic polymerization of an adhesive, coating film formation, action of sealing or caulking agent, detergent, etc.

The base formed in the present invention can be used as a catalyst for the polymerization reaction of anionic polymerizable monomers. Any kinds of the anionic polymerizations can employ the process of the invention. Thus, the anionic polymerization employing the process can be utilized in various products, such as adhesives, coating agents, sealing or caulking materials.

The process of the present invention can also be applied to other products containing a base component, such as detergents, mold killers, etc. In these cases, the products preferably are in the form of a binary system consisting of one component containing the base precursor and the other containing the catalyst for the decomposition reaction of the base precursor. When both components are mixed together (and then preferably heated) for the use of the product, a base can be formed according to the invention. As a result, these products can be made neutral, safe and stable in the period of their storage.

In the diazotype photographic process, the remaining diazonium salt within the unexposed area and a coupler are subjected to a coupling reaction to form an azo dye, as shown in the following reaction formula.

$N_2$ ↑ + ArX (Colorless)
(or ArOH in the presence of $H_2O$)
Light
$ArN_2^{\oplus}.X^{\ominus}$ + Ar'OH
(Diazonium salt) (Coupler)
Alkali
ArN=N—Ar'OH
(Azo dye)

When the present invention is utilized in the diazotype photographic process, for example, to a dry process, the base precursor and the catalyst together with the diazonium salt are added to a diazotype light-sensitive paper. The base precursor and the catalyst are preferably separated from each other in the light-sensitive paper. The diazotype light-sensitive paper can be exposed and then heated for development to obtain an azo dye image. In a conventional diazotype photographic process employing a heat development, ammonium carbonate or hexamethylenetetramine is frequently used as an alkaliforming agent. In this conventional process, the developing time is relatively long and the light-sensitive paper has a problem with respect to the stability. Where the present invention is applied to the process, the image can be rapidly formed and the light-sensitive paper is improved in the stability.

In a conventional silver salt photographic process, the development (i.e., an oxidation-reduction reaction between silver halide and a developing agent) is carried out under an alkaline condition. Where the base precursor and the catalyst are contained in a light-sensitive material, the development can be carried out only by heating after exposure. The base precursor and the catalyst are preferably separated from each other in the light-sensitive material. Therefore, each of the base precursor and the catalyst is preferably contained in each of different layers. The different layers may be provided on either separate support or the same support. For example, when the base precursor is contained in a light-sensitive material and the catalyst is contained in a sheet material for development, both of the materials can be arranged together in layers and then heated in the development process. Alternatively, the base precursor and the catalyst are separated from each other in the same layer by incorporating at least one component in oil droplets of emulsion, in dispersed solid particles, or in microcapsules.

Further, the process of the present invention can be advantageously utilized in the light-sensitive material comprising a light-sensitive layer containing silver halide, a reducing agent and a polymerizable compound provided on a support. This light-sensitive material can be used in an image forming method in which a latent image of silver halide is formed, and then the polymerizable compound is polymerized to form the corresponding image.

Example of the image forming methods are described in Japanese Patent Publication Nos. 45(1970)-11149 (corresponding to U.S. Pat. No. 3,697,275), 47(1972)-20741 (corresponding to U.S. Pat. No. 3,687,667) and 49(1974) -10697, and Japanese Patent Provisional Publication Nos. 57(1982)-138632, 57(1982)-142638, 57(1982)-176033, 57(1982)-211146 (corresponding to U.S. Pat. No. 4,557,997), 58(1983)-107529 (corresponding to U.S. Pat. No. 4,560,637), 58(1983)-121031 (corresponding to U.S. Pat. No. 4,547,450) and 58(1983)-169143. In these image forming methods, when the exposed silver halide is developed using a developing solution, the polymerizable compound is induced to polymerize in the presence of an oxidized reducing agent to form a polymer image. Thus, these methods need a wet development process employing a developing solution. Therefore the process takes a relatively long time for the operation.

An improved image forming method employing a dry process is described in Japanese Patent Provisional Publication Nos. 61(1986)-69062 and 61(1986)-73145 (the contents of both publications are described in U.S. Pat. No. 4,629,676 and European Patent Provisional Publication No. 0174634A2). In this image forming method, a recording material (i.e., light-sensitive material) comprising a light-sensitive layer containing a light-sensitive silver salt (i.e., silver halide), a reducing agent, a cross-linkable compound (i.e., polymerizable compound) and a binder provided on a support is imagewise exposed to form a latent image, and then the material is heated to polymerize within the area where the latent image of the silver halide has been formed. The above method employing the dry process and the light-sensitive material employable for such method are also described in Japanese Patent Provisional Publication Nos. 61(1986)-183640, 61(1986)-188535 and 61(1986)-228441.

The above-mentioned image forming methods are based on the principle in which the polymerizable compound is polymerized within the area where a latent image of the silver halide has been formed.

Japanese Patent Provisional Publication No. 61(1986) -260241 describes another image forming method in which the polymerizable compound within the area where a latent image of the silver halide has not been formed is polymerized. In this method, when the material is heated, the oxidized reducing agent functions as polymerization inhibitor within the area where a latent image of the silver halide has been formed, and the polymerizable compound within the other area is polymerized.

The polymerization reaction in the above-mentioned image-forming methods smoothly proceeds under an alkaline condition. Therefore, a base or a base precursor may be contained in the light-sensitive layer of the light-sensitive material. Examples of the base and base precursor are described in Japanese Patent Provisional Publication No. 61(1986)-73145 (corresponding to U.S. Pat. No. 4,629,676 and European Patent Provisional Publication No. 0174634A2). Where a base or base precursor is contained in the light-sensitive layer prior to a heat development process, the light-sensitive material tends to lower in sensitivity and sharpness of the obtained image (especially in the case that a base is used). Further, the base precursors described in the above Publication are incomplete with respect to the stability in the preservation or the rate of the decomposition (i.e., releasing a base) in the heat development process.

The present invention further provides a light-sensitive material which gives a clear image in a development process.

The light-sensitive material of the present invention comprises a light-sensitive layer containing silver halide, a reducing agent and a polymerizable compound on a support, wherein the light-sensitive layer further contains a base precursor having the following formula (I) or (II):

$$(R^1—C≡C—CO_2H)_x.B \qquad (I)$$

$$R^2(—C≡C—CO_2H)_2.B_y \qquad (II)$$

wherein $R^1$ is a monovalent group selected from the group consisting of hydrogen, an alkyl group, a cycloalkyl group, an alkenyl group, an alknyl group, an aryl group, a heterocyclic group, an aralkyl group, an acyl group, an alkoxycarbonyl group, carbamoyl, $—CO_2M$ (M is an alkali metal) and $—CO_2H.B$, each of which may have one or more substituent groups; $R^2$ is a divalent group selected from the group consisting of an alkylene group, an arylene group and a divalent heterocyclic group, each of which may have one or more substituent groups; B is an organic base; x is 1 when B is a monoacidic base, and x is 2 when B is a diacidic base; and y is 2 when B is a monoacidic base, and y is 1 when B is a diacidic base, and a catalyst for decomposition of the base precursor, the catalyst being selected from the group consisting of silver, a silver compound, copper and a copper compound.

The light-sensitive material of the invention characterized in that the light-sensitive layer contains the catalyst for decomposition of a base precursor in addition to the base precursor having the formula (I) or (II).

Some examples of the base precursor having the formula (I) or (II) have been described in Japanese Patent Provisional Publication No. 61(1986)-73145 (corresponding to U.S. Pat. No. 4,629,676 and European Patent Provisional Publication No. 0174634A2). As described in the Publication, these base precursors can be preferably employed in the light-sensitive material comprising a light-sensitive layer containing silver halide, a reducing agent and a polymerizable compound on a support. However, the present inventors have noted that while the base precursor having the formula (I) or (II) is very stable in the preservation, it is incomplete with respect to the rate of the decomposition (i.e., releasing a base) in the heat development process.

The present inventors have found that silver, a silver compound, copper and a copper compound function as excellent catalysts for the decomposition reaction (base forming reaction) of the base precursor having a formula (I) or (II).

In the heat development process of the light-sensitive material of the invention, the rate of the decomposition of the base precursor is accelerated by the catalyst to form a base more rapidly. Therefore, the light-sensitive material of the invention can give a clear image in a heat development process, because the polymerization reaction proceeds rapidly and smoothly by the formed base. Further, the light-sensitive material can give a clear image, even if the heat development process is carried out at a lower temperature or in a shorter time.

In the light-sensitive material, the above-mentioned base precursors can be used singly or in combination. The base precursor is preferably used in an amount of 0.01 to 10 $g/m^2$ in the light-sensitive layer, and more preferably used in an amount of 0.1 to 3 $g/m^2$.

The above-mentioned catalyst can also be used singly or in combination. The catalyst is preferably used in an amount of 0.001 to 1 mole based on the amount of 1 mole of the base precursor in the light-sensitive layer.

In the light-sensitive material of the invention, the light-sensitive layer preferably further contains a free ligand.

The free ligand has a function of trapping silver ion or copper ion which is liberated from the catalyst during the preservation of the light-sensitive material. Therefore, the base precursor in the light-sensitive layer is protected by the free ligand from the silver or copper ion. On the other hand, the free ligand does not appreciably inhibit the function of the catalyst, because in the heat development process, a large and sufficient amount of silver or copper ion is liberated from the catalyst. As a result, the light-sensitive material containing a free ligand can give a clear image, even if the material is preserved for a long term or under a severe conditions.

The ligand in the present specification means a compound (complexing agent) having a function of coordinating silver or copper ion. However almost all of the compounds referred to as "ligand" have the function (especially there is no limitation at all with respect to the ligand of coordinating copper ion). Therefore the ligand used in the light-sensitive material can be arbitrarily selected from the known compound.

Examples of the ligand which are preferably used in the light-sensitive material are described below.

(1) Ligands having oxygen as the coordinating atom include:

a 1,2-dicarbonyl compound (e.g., oxalic acid), a 1,3-dicarbonyl compound (e.g., acetylacetone, benzoylacetone), an aromatic polyhydroxyl compound (e.g., catechol, pyrogallol) and an aromatic hydroxycarbonyl compound (e.g., salycylic acid, salicylaldehyde).

(2) Ligands having nitrogen as the coordinating atom include:

an aliphatic amine (e.g., n-butylamine, ethylene diamine), an aromatic amine (e.g., aniline, o-phenylene diamine), a heterocyclic compound (e.g., bipyridiine, o-phenanthroline) and an α-dioxime (e.g., dimethylglyoxime).

(3) Ligands having oxygen and nitrogen as the coordinating atoms include:

an aminoalcohol (e.g., triethanolamine, monoethanolamine), an oxime (e.g., salicylaldoxime), a heterocyclic compound (e.g., 2-pyridinecarboxylic acid, 8-hydroxyquinoline), an aromatic azo compound (e.g., 1-(2-pyridylazo)-2naphthol), a complexon (e.g., ethylenediaminetetraacetic acid, nitrilotriacetic acid) and an amino acid (e.g., glycine, alanine, serine).

(4) Ligands having atoms other than oxygen and nitrogen as the coordinating atom include:

a ligand having sulfur as the coordinating atom (e.g., thiourea).

Among these ligands, those having oxygen and nitrogen as the coordinating atoms (3) are preferred. The oxime, heterocyclic compound and complexon are more preferred. The ligand preferably is a multiple-dentate ligand (chelating ligand).

The process for synthesis of these ligands is stated in Keihei Ueno (ed.), Chelate Chemistry, Vol. 5, Chap. 1, 1-365 (in Japanese, published by Nankodo, 1975). The other ligands stated in the literature can also be used in the light-sensitive materials without specific limitation.

In order to set the ligand free in the light-sensitive layer, various embodiments of the light-sensitive layer can be employed.

In the first embodiment, an excess amount (based on silver or copper atom contained in the catalyst) of the ligand is added to the light-sensitive layer. In this case, the light-sensitive layer contains a catalyst, which is a complex of silver or copper, and a free ligand. Where the silver or copper compound (salt or covalent-bonded compound) is insoluble in water, the compound is partially transformed to a complex by the ligand in the light-sensitive layer. When silver or copper ion is liberated from the catalyst (complex, salt or covalent compound) during the preservation of the light-sensitive material, the ion is immediately trapped by the free ligand. Therefore, the base precursor is scarcely decomposed by the liberated silver or copper ion.

In the second embodiment, where the catalyst does not form a complex with the ligand, for example in the case that the catalyst is metallic silver or copper, all of the ligand added to the light-sensitive layer should be free. In this case, the preservability of the lightsensitive material is also improved, because the free ligand traps silver or copper ion formed by oxidation of the metal during the preservation of the light-sensitive material.

In the third embodiment, the catalyst is separated from the ligand in the light-sensitive layer to set the ligand free. In this case, the base precursor is preferably arranged on the side of the ligand. Where the catalyst is separated from the base precursor and the free ligand, silver or copper ion liberated from the catalyst scarcely comes into contact with the base precursor by a separating means during the preservation of the light-sensitive material, and even if the ion invades the side of the base precursor beyond the separating means, it is immediately trapped by the free ligand. Thus, the base precursor is almost completely protected from the liberated ion. Another advantage of the third embodiment is that even if a small amount of the ligand is used, it can be set free in the light-sensitive layer. As mentioned above, the third embodiment is most preferred.

In the light-sensitive material of the invention, the light-sensitive layer preferably contains the free ligand in an amount of 0.01 to 10 mole based on the amount of 1 mole of the catalyst, and more preferably in an amount of 0.05 to 1 mole.

The separating means employed in the third embodiment are described below.

Even in the case that the free ligand is not contained in the light-sensitive layer, it is also effective that the catalyst is separated from the base precursor in the light-sensitive layer. Where the catalyst is separated from the base precursor, silver or copper ion liberated from the catalyst scarcely comes into contact with the base precursor by a separating means during the preservation of the light-sensitive material. Therefore, the following separating measures are also preferably used in the light-sensitive layer only to separate the catalyst from the base precursor.

An example of the separating measure is that the catalyst or the base precursor is contained in microcapsules which are dispersed in the light-sensitive layer. Another example is that the catalyst, the base precursor and/or the free ligand are contained independently in solid particles which are dispersed in the light-sensitive layer. The solid particles are composed of the above component and an inactive diluent material which is miscible with the component.

Among the catalyst, the base precursor and the free ligand, the catalyst is most preferably contained in the microcapsules or the solid particles, because the catalyst generally is insoluble in water and thus it is easy to incorporate the catalyst into the mirocapsules or the particles, while the others generally are soluble in water. When the catalyst is contained in the microcapsules or the solid particles, the others are arranged outside of the microcapsules or the particles.

There is no specific limitation with respect to shell material of the microcapsule containing the catalyst, and various known materials such as polymers which are employed in the conventional microcapsules can be employed as the shell material. Examples of the process for the preparation of the microcapsules include a process utilizing coacervation of hydrophilic shell-forming materials as described in U.S. Pat. Nos. 2,800,457 and 2,800,458; an interfacial polymerization process as described in U.S. Pat. No. 3,287,154, U.K. Pat. No. 990,443 and Japanese Patent Publication Nos. 38(1963)-19574, 42(1967)-446 and 42(1967)-771; a process utilizing precipitation of polymers as described in U.S. Pat. Nos. 3,418,250 and 3,660,304; a process of using isocyanate-polyol shell materials as described in U.S. Pat. No. 3,796,669; a process of using isocyanate shell materials as described in U.S. Pat. No. 3,914,511; a process of using urea-formaldehyde or urea-formaldehyde-resorcinol shell-forming materials as described in U.S. Pat. Nos. 4,001,140, 4,087,376 and 4,089,802; a process of using melamine-formaldehyde resins hydroxypropyl cellulose or like shell-forming materials as described in U.S. Pat. No. 4,025,455; an in situ process untilizing polymerization of monomers as described in U.K. Pat. No. 867,797 and U.S. Pat. No. 4,001,140; an electrolytic dispersion and cooling process as described in U.K. Pat. Nos. 952,807 and 965,074; a spray-drying process as described in U.S. Pat. No. 3,111,407 and U.K. Pat. No. 930,422.

It is preferable, though not limitative, that the microcapsule is prepared by emulsifying core materials containing the catalyst and an oil and forming a polymeric membrane (i.e., shell) over the core materials.

Examples of the oils include organic solvents which are used as solvents in emulsifying and dispersing hydrophobic compounds. Volatile organic solvents having a boiling point of not higher than 100° C. are preferably employed as the oil, because they can be easily removed simultaneously with or after preparation of the microcapsules. Examples of the volatile organic solvents include ethanol, acetone, methyl ethyl ketone, methyl acetate, ethyl acetate, methylene chloride and chloroform.

The microcapsule containing the catalyst preferably has a shell material which can be ruptured under a heating condition. More concretely, the shell material preferably has a melting point or a softening point of 60° to 200° C. The temperature of the melting or softening is preferably not higher than the melting point of the catalyst contained in the microcapsule.

Example of the shell material which can be ruptured under a heating condition is a wax having a melting point or a softening point of 60° to 200° C. Known waxes such as a natural wax, petroleum wax and sythetic wax can be employed as the shell material of the microcapsule.

Examples of waxes employable as the shell material of the microcapsule containing the catalyst in the light-sensitive material of the invention are shown as follows:

(1) natural wax: vegetable wax (e.g., candelilla wax, carnauba wax, rice wax and Japan wax), animal wax (e.g., beeswax, lanolin, spermaceti), mineral wax (e.g., montan wax, ozokerite, ceresin wax);

(2) petroleum wax: paraffin wax, microcrystalline wax; and (3) synthetic wax: coal-originating synthetic wax, polyethylene wax, Fischer-Tropsch wax, fatty compound-orginating synthetic wax (e.g., cured castor oil, aliphatic amide, ketone, amine, imide, esters).

Another example of the shell material having a melting point or a softening point of 60° to 200° C. is a polyurea resin and/or polyurethane resin.

A number of processes for the preparation of microcapsules having a shell of a polyurea resin and a polyurethane are known as mentioned above. These processes are also employable for the preparation of the microcapsule containing the catalyst of the invention.

In the present invention, the terms "polyurea resin" and "polyurethane resin" are not construed to indicate polymers containing, respectively, the urea bondings only or the urethane bondings only. For instance, the polyurethane resin include a polyurethane resin in which certain portions of the urethane bondings are replaced with urea bondings. This is also applied to the polyurea resin.

Examples of the polyisocyanate compounds, polyamine compounds, and polyol compounds include the following compound.

The polyisocyanate can be a diisocyanate compound such as m-phenylene diisocyanate, p-phenylene diisocyanate, 2,6-tolylene diisocyanate, 2,4-tolylene diisocyanate, naphthalene-1,4-diisocyanate, diphenylmethane-4,4'-diisocyanate, 3,3'-dimethoxy-4,4'-biphenyl diisocyanate, 3,3'dimethyl-4,4'-diisocyanate, xylylene-1,4-diisocyanate, xylylene-1,3-diisocyanate, 4.4'-diphenylpropane diisocyanate, trimethylene diisocyanate, hexamethylene diisocyanate, propylene-1,2-diisocyanate, butylene-1,2-diisocyanate, ethylidyne diisocyanate, cyclohexylene-1,2-diisocyanate or cyclohexylene-1,4-diisocyanate; a triisocyanate compound such as 4,4',4''-triphenylmethane triisocyanate, toluene-2,4,6-triisocyanate or polymethylene polyphenyl triisocyanate; a tetraisocyanate compound such as 4,4'-dimethyldiphenylmethane-2,2',5,5'-tetraisocyanate; or a polyisocyanate prepolymer such as an addition compound of hexamethylene diisocyanate and hexanetriol, an addition compound of 2,4-tolylene diisocyanate and catechol or an addition compound of tolylene diisocyanate and trimethylolpropane.

The polyamine compound can be ethylenediamine, trimethylenediamine, tetramethylenediamine, pentamethylenediamine, hexamethylenediamine, p-phenylenediamine, m-phenylenediamine, piperazine, 2-methylpiperazine, 2,5-dimethylpiperazine, 2-hydroxytrimethylenediamine, diethylaminopropylamine, tetraethylenepentamine, or an amine adduct of an epoxy compound.

The polyol compound can be ethylene glycol, 1,4-butanediol, chatecol, resorcinol, hydroquinone, 1,2-dihydroxy-4-methylbenzene, 1,3-dihydroxy-5-methylbenzene, 3,4-dihydroxy-1-methylbenzene, 3,5-dihydroxy-1-methylbenzene, 2,4-dihydroxyethylbenzene, 1,3-naphthalene-diol, 1,5-naphthalenediol, 2,7-naphthalenediol, or 2,3-naphthalenediol. Water can be also employed in place of the polyol compound.

There is also no specific limitation with respect to the material which forms particles of uniform solid solution with the catalyst, so long as the material and the catalyst are soluble in each other. For example, the wax, which is employed as the shell material of the microcapsuel as mentioned above, can be also employed as the material.

The material which is miscible with the catalyst and can form an uniform solid solution with the catalyst is preferably a hot-melt solvent having a melting point of 30° to 200° C. "Hot-melt solvent" is defined as a material which is solid at the ambient temperature and which melts to be a liquid solvent at an elevated temperature. The inventors have found that the hot-melt solvent has a function of accelerating the decomposition of the base precursor in a heat development process. In more detail, when the light-sensitive material is heated, the base precursor is dissolved in the hot-melt solvent to accelerate the decomposition reaction. Further, the hot-melt solvent has another function of improving the preservability of the light-sensitive material. Therefore, it is also effective that the hot-melt solvent is incorporated into the light-sensitive layer, even in the case that the free ligand is not contained in the light-sensitive layer, no separating means is employed or microcapsules are used as the separating means. In this case, the hot-melt solvent preferably is in the form of fine particles which are dispersed in the light-sensitive layer.

The hot-melt solvent has a melting point of 30° to 200° C., and preferably of 50° to 150° C.

The hot-melt solvent preferably is a compound having a polar group. The polar group preferably has a function of dissolving the base precursor when heated. Examples of the compound having a polar group and a melting point of 30 to 200° C. include a carboxylic acid amide derivative, a sulfonamide derivative, a phosphoric acid amide derivative, a ketone, an ester, an ether, an urea derivative, an urethane and a polyhydroxyl compound. Among them, a carboxylic acid amide derivative, an urea derivative and a polyhydroxyl compound are preferred.

Examples of the hot-melt solvent which are preferably used in the light-sensitive material are shown as follows:

(A) polyhydroxyl compound: sorbitol, mannitol, dulcitol, pentaerythritol, trimethylolethane, trimethylolpropane, hexanediol, cyclohexanediol, ethylene glycol, propylene glycol, saponin, vanilline, decanediol;

(B) amide: acetamide, propionamide, benzenesulfonamide, benzamide;

(C) urea derivative: methylurea, dimethylurea (e.g., 1,3-dimethylurea), ethylurea, diethylurea, n-butylurea, butylurea, dimethylolurea, tetramethylurea, phenylurea, benzoylurea, 1,1-diethylurea.

The other examples of the hot-melt solvent (including those classified into (A) to (C)) are described hereinafter.

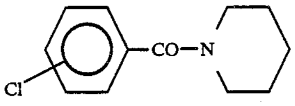
(S-1)

-continued

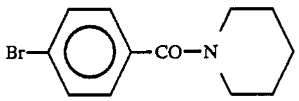
(S-2)

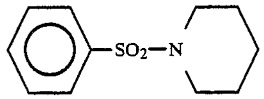
(S-3)

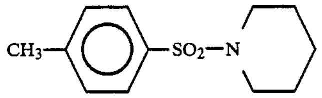
(S-4)

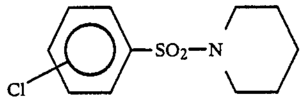
(S-5)

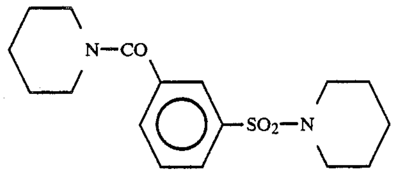
(S-6)

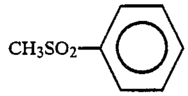
(S-7)

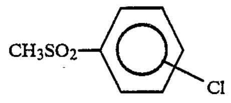
(S-8)

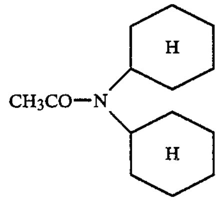
(S-9)

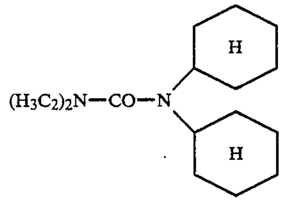
(S-10)

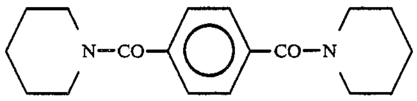
(S-11)

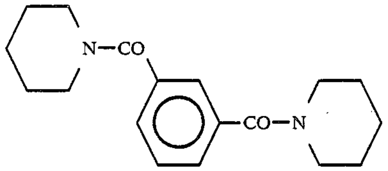
(S-12)

-continued
(S-13)
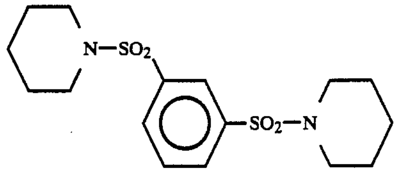
(S-14)
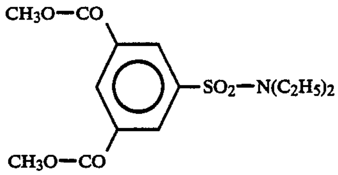
(S-15)
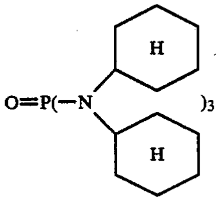
(S-16)
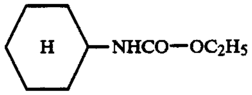
(S-17)
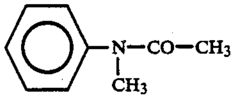
(S-18)
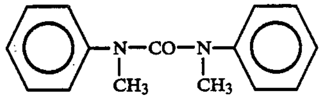
(S-19)
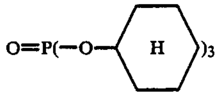
(S-20)
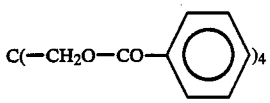
(S-21)
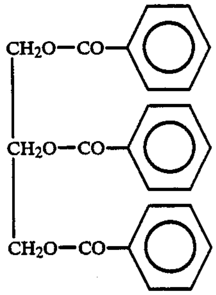
-continued
(S-22)
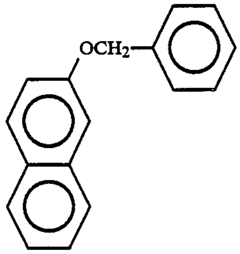
(S-23)
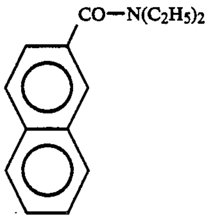
(S-24)
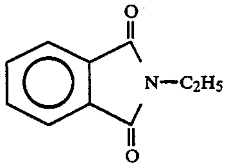
$H_2N-SO_2-N(C_3H_7)_2$ (S-25)
(S-26)
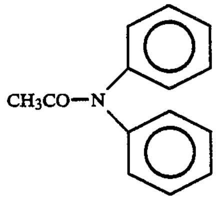
(S-27)
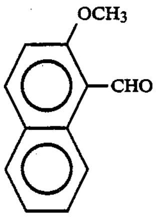
(S-28)
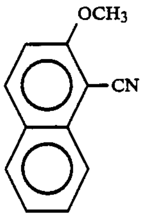
(S-29)
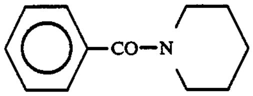

-continued (S-30)

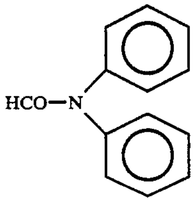

(S-31)

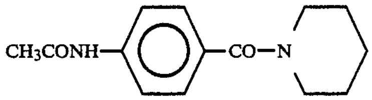

(S-32)

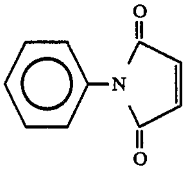

(S-33)

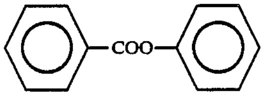

(S-34)

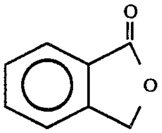

(S-35)

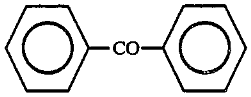

(S-36)

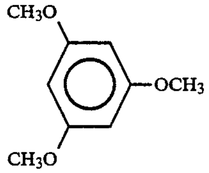

$n\text{-}C_{16}H_{33}OH$ (S-37)

$n\text{-}C_{18}H_{37}OH$ (S-38)

These hot-melt solvents can be used singly or in combination. Where the hot-melt solvent is employed to form uniform prticles of solid solution with the catalyst, the hot-melt solvent is preferably used in an amount of 3 to 30 weight % of the light-sensitive layer, and more preferably used in amount of 5 to 20 weight %. Where the hot-melt solvent is simply incorporated into the light-sensitive layer, the hot-melt solvent is preferably used in an amount of 0.01 to 10 g/m$^2$ in the light-sensitive layer.

The particles of solid solution made of the catalyst and a diluent material can be prepared by melting the catalyst and the material upon heating to obtain an uniform solution, cooling the solution to solidify it, and then grinding the obtained solid. Alternatively, the particles of solid solution can be prepared by dispersing the uniform solution into a cool liquid (e.g., water).

The silver halide, the reducing agent, the polymerizable compound and the support which constitute the light-sensitive material are described below. Thus composed material is referred hereinafter to as "light-sensitive material".

There is no specific limitation with respect to silver halide contained in the light-sensitive layer of the light-sensitive material. Examples of the silver halides include silver chloride, silver bromide, silver iodide, silver chlorobromide, silver chloroiodide, silver iodobromide and silver chloroiodobromide in the form of grains.

The halogen composition of individual grains may be homogeneous or heterogeneous. The heterogeneous grains having a multilayered structure in which the halogen composition varies from the core to the outer shell (see Japanese Patent Provisional Publication Nos. 57(1982)-154232, 58(1983)-108533, 59(1984) -48755 and 59(1984)-52237, U.S. Pat. No. 4,433,048, and European Pat. No. 100,984) can be employed. A silver halide grain having a core/shell structure in which the silver iodide content in the shell is higher than that in the core can be also employed.

There is no specific limitation on the crystal habit of silver halide grains. For example, a tubular grain having an aspect ratio of not less than 3 can be emplyed.

Two or more kinds of silver halide grains which differ in halogen composition, crystal habit, grain size, and/or other features from each other can be used in combination.

There is no specific limitation on grain size distribution of silver halide grains. For example, the silver halide grains having such a grain size distribution that the coefficient of the variation is not more than 20 % can be employed.

The silver halide grains ordinarily have a mean size of 0.001 to 5 $\mu$m, more preferably 0.001 to 2 $\mu$m.

The total silver content (including silver halide and an organic silver salt which is one of optional components) in the light-sensitive layer preferably is in the range of from 0.1 mg/m$^2$ to 10 g/m$^2$. The silver content of the silver halide in the light-sensitive layer preferably is not more than 0.1 g/m$^2$, more preferably in the range of from 1 mg to 90 mg/m$^2$.

The reducing agent employed in the light-sensitive material has a function of reducing the silver halide and/or a function of accelerating or restraining a polymerization of the polymerizable compound. Examples of the reducing agents having these functions include various compounds, such as hydroquinones, catechols, p-aminophenols, p-phenylenediamines, 3-pyrazolidones, 3-aminopyrazoles, 4-amino-5-pyrazolones, 5-aminouracils, 4,5-dihydroxy-6-aminopyrimidines, reductones, aminoreductones, o- or p-sulfonamidophenols, o- or p-sulfonamidonaphthols, 2-sulfonamidoindanones, 4-sulfonamido-5-pyrazolones, 3-sulfonamidoindoles, sulfonamidopyrazolobenzimidazoles, sulfonamidopyrazolotriazoles, $\alpha$-sulfonamidoketones, hydrazines, etc. Depending on the nature or amount of the reducing agent, the polymerizable compound within either the area where a latent image of the silver halide has been formed or the area where a latent image of the silver halide has not been formed can be polymerized. In the developing system in which the polymerizable compound within the area where the latent image has not been formed is polymerized, 1-phenyl-3-pyrazoli done is preferably employed as the reducing agent.

The light-sensitive materials employing the reducing agent having these functions (including compounds referred to as developing agent, hydrazine derivative or precursor of reducing agent) are described in Japanese Patent Provisional Publication Nos. 61(1986)-83640, 61(1986)-188535 and 61(1986)-228441. These reducing agents are also described in T. James, "The Theory of the Photographic Process", 4th edition, 291–334 (1977), Research Disclosure No. 17029, 9–15 (June 1978), and Research Disclosure No. 17643, 22–31 (Dec. 1978). The reducing agents described in the these publications can be employed in the light-sensitive material of the present invention. Thus, "the reducing agents(s)" in the present specification means to include all of the reducing agents described in the above mentioned publications and applications.

These reducing agents can be used singly or in combination. In the case that two or more reducing agents are used in combination, certain interactions between these reducing agents may be expected. One of the interactions is for acceleration of reduction of silver halide (and/or an organic silver salt) through so-called superadditivity. Other interaction is for a chain reaction in which an oxidized state of one reducing agent formed by a reduction of silver halide (and/or an organic silver salt) induces or inhibits the polymerization of the polymerizable compound via oxidation-reduction reaction with other reducing agent. Both interactions may occur simultaneously. Thus, it is difficult to determine which of the interactions has occurred in practical use.

Examples of these reducing agents include pentadecylhydroquinone, 5-t-butylcatechol, p-(N,N-diethylamino)phenol, 1-phenyl-4-methyl-4-hydroxymethyl-3-pyrazolidone, 1-phenyl-4-methyl-4-heptadecylcarbonyloxymethyl -3-pyrazolidone, 2-phenylsulfonylamino-4-hexadecyloxy-5-t-octylphenol, 2-phenylsulfonylamino-4-t-butyl-5-hexadecyloxyphenol, 2-(N-butylcarbamoyl)-4-phenylsulfonylaminonaphtol, 2-(N-methyl-N-octadecylcarbamoyl)-4-sulfonylaminonaphthol, 1-acetyl-2-phenylhydrazine, 1-acetyl-2-(p- or o-aminophenyl)hydrazine, 1formyl-2-(p- or o-aminophenyl)hydrazine, 1-acetyl-2-(p- or o-methoxyphenyl)-hydrazine, 1-lauroyl-2-(p- or o-aminophenyl)hydrazine, 1-tri -trityl-2-(2,6-dichloro-4-cyanophenyl)hydrazine, 1-trityl-2-phenylhydrazine, 1-phenyl-2-(2,4,6-trichlorophenyl)hydrazine, 1-{2-(2,5-di-tert-pentylphenoxy)-butyloyl}-2-(p- or o-aminophenyl)hydrazine, 1-{2-(2,5-di-t-pentylphenoxy)butyloyl}-2-(p- or o-aminophenyl)-hydrazine pentadecylflurocaprylate salt, 3-indazolinone, 1-(3,5-dichlorobenzoyl)-2phenylhydrazine, 1-trityl-2-[{(2-N-butyl-N-octylsulfamoyl) -4-methanesulfonyl}phenyl]hydrazine, 1-}4-2,5-di-tert-pentylphenoxy)butyloyl}-2-(p- or o -methoxyphenyl)hydrazine, 1-(methoxycarbonylbenzohydryl)-2-phenylhydrazine, 1-formyl-2-[4-{2-(2,4-di-tert -pentylphenoxy)-butylamide}phenyl]hydrazine, 1-acetyl-2-[4-{2-(2,4-di -tert-pentylphenoxy)butylamido}phenyl]hydrazine, 1-trityl-2-[{2,6-dichloro-4-(N,N-di -2-ethylhexyl)carbamoyl}phenyl]hydrazine, 1-(methoxycarbonylbenzohydryl)-2-(2,4-dichlorophenyl)hydrazine, 1-trityl-2-[{2-(N-ethyl- 1-benzoyl-2-tritylhydrazine, 1-(4-butoxybenzoyl)-2-tritylhydrazine, 1-(2,4-dimethoxybenzoyl)-2-tritylhydrazine, 1-(4-dibutylcarbamoylbenzoyl)-2-tritylhydrazine and 1-(1-naphthoyl)-2-tritylhydrazine.

The amount of the reducing agent in the light-sensitive layer preferably ranges from 0.1 to 1,500 mole % based on the amount of silver (contained in the above-mentioned silver halide and an organic silver salt).

There is no specific limitation with respect to the polymerizable compound, and any known polymerizable compounds including monomers, oligomers and polymers can be contained in the light-sensitive layer. In the case that heat development (i.e., thermal development) is utilized for developing the light-sensitive material, the polymerizable compounds having a relatively higher boiling point (e.g., 80° C. or higher) that are hardly evaporated upon heating are preferably employed. In the case that the light-sensitive layer contains a color image forming substance, the polymerizable compounds are preferably cross-linkable compounds having plural polymerizable groups in the molecule, because such cross-linkable compounds favorably serve for fixing the color image forming substance in the course of polymerization hardening of the polymerizable compounds.

The polymerizable compound employable for the light-sensitive material are described in the above-mentioned and later-mentioned publications concerning the light-sensitive material.

Preferred polymerizable compounds employable for the light-sensitive material are compounds which are polymerizable through addition reaction or ring-opening reaction. Preferred examples of the compounds being polymerizable through addition reaction include compounds having an ethylenic unsaturated group. Preferred examples of the compounds being polymerizable through ring-opening reaction include the compounds having an epoxy group. Among them, the compounds having an ethylenic unsaturated group are preferred.

Examples of compounds having an ethylenic unsaturated group include acrylic acid, salts of acrylic acid, acrylic esters, acrylamides, methacrylic acid, salts of methacrylic acid, methacrylic esters, methacrylamide, maleic anhydride, maleic esters, itaconic esters, styrene, styrene derivatives, vinyl ethers, vinyl esters, N-vinyl heterocyclic compounds, allyl ethers, allyl esters, and compounds carrying a group or groups corresponding to one or more of these compounds.

Concrete examples of the acrylic esters include n-butyl acrylate, cyclohexyl acrylate, 2-ethylhexyl acrylate, benzyl acrylate, furfuryl acrylate, ethoxyethoxy acrylate, dicyclohexyloxyethyl acrylate, nonylphenyloxyethyl acrylate, hexanediol diacrylate, butanediol diacrylate, neopentylglycol diacrylate, trimethylolpropane triacrylate, pentaerythritol tetraacrylate, dipentaerythritol pentaacrylate, diacrylate of polyoxyethylenated bisphenol A, polyacrylate of hydroxypolyether, polyester acrylate, and polyurethane acrylate.

Concrete examples of the methacrylic esters include methyl methacrylate, butyl methacrylate, ethylene glycol dimethacrylate, butanediol dimethacrylate, neopentylglycol dimethacrylate, trimethylolpropane trimethacrylate, pentaerythritol trimethacrylate, pentaerythritol tetramethacrylate, and dimethacrylate of polyoxyalkylenated bisphenol A.

The polymerizable compounds can be used singly or in combination of two or more compounds. For example, a mixture of two or more polymerizable compounds can be employed. Further, compounds formed by bonding a polymerizable group such as a vinyl group or a vinylidene group to a reducing agent or a color image forming substance are also employed as the polymerizable compounds. The light-sensitive materials employing these compounds which show functions as both the reducing agent and the polymerizable compound, or of the color image forming substance and the polymerizable compound are included in embodiments of the invention.

The amount of the polymerizable compound for incorporation into the light-sensitive layer preferably ranges from 5 to $1.2\times10^5$ times (by weight) as much as the amount of silver halide, more preferably from 10 to $1\times10^4$ times as much as the amount of silver halide.

The light-sensitive material can be prepared by arranging a light-sensitive layer containing the above-mentioned components on a support. There is no limitation with respect to the support. In the case that heat development is utilized in the use of the light-sensitive material, the material of the support preferably is resistant to heat given in the processing stage. Examples of the material employable for the preparation of the support include glass, paper, fine paper, coat paper, synthetic paper, metals and analogues thereof, polyester, acetyl cellulose, cellulose ester, polyvinyl acetal, polystyrene, polycarbonate, polyethylene terephthalate, and paper laminated with resin or polymer (e.g., polyethylene). In the case that a porous material, such as paper is employed as the support, the porous support preferably has such a surface characteristic that a filtered maximum waviness of not less than 4 μm is observed in not more than 20 positions among 100 positions which are determined at random on a filtered waviness curve obtained according to JIS-B-0610.

Various embodiments of the light-sensitive materials, optional components which may be contained in the light-sensitive layer, and auxiliary layers which may be optionally arranged on the light-sensitive materials are described below.

The polymerizable compound is preferably dispersed in the form of oil droplets in the light-sensitive layer. Other components in the light-sensitive layer, such as silver halide, the reducing agent may be also contained in the oil droplets.

The oil droplets of the polymerizable compound are preferably prepared in the form of microcapsules. The mirocapsule containing the polymerizable compound differs from that containing the catalyst, in the case that the catalyst is incorporated into microcapsules. There is no specific limitation on preparation of the microcapsules.

There is also no specific limitation on shell material of the microcapsule, and various known materials such as polymers which are employed in the conventional microcapsules can be employed as the shell material. Examples of the shell material include polyamide resin and/or polyester resin, polyurea resin and/or polyurethane resin, aminoaldehide resin, gelatin, epoxy resin, a complex resin containing polyamide resin and polyurea resin, a complex resin containing polyurethane resin and polyester resin.

The mean size of the microcapsule preferably ranges from 0.5 to 50 μm, more preferably 1 to 25 μm, most preferably 3 to 20 μm. In the case that silver halide grains are contained in the microcapsule, the mean grain sized of the silver halide grains preferably is not more than the 5th part of the mean size of the microcapsules, more preferably is not more than the 10th part. It is observed that when the mean sized of the microcapsules is not less than 5 times as much as the mean grain size of silver halide grains, even and uniform image can be obtained.

In the case that silver halide grains are contained in the microcapsule, the silver halide grains are preferably arranged in the shell material of the microcapsules.

Further, two or more kinds of the microcapsules differing from each other with respect to at least one of the silver halide, the polymerizable compound and the color image forming substance can be employed. Furthermore, three or more kinds of the microcapsules differing from each other with respect to the color image forming substance is preferably employed to form a full color image.

The light-sensitive layer can further contain optional components such as color image forming substances, sensitizing dyes, organic silver salts, various kinds of image formation accelerators, thermal polymerization inhibitors, thermal polymerization initiators, development stopping agents, fluorescent brightening agents, discoloration inhibitors, antihalation dyes or pigments, antiirradiation dyes or pigments, matting agents, antismudging agents, plasticizers, water releasers, binders, photo polymerization initiators and solvents of the polymerizable compound.

There is no specific limitation with respect to the color image forming substance, and various kinds of substances can be employed. Thus, examples of the color image forming substance include both colored substance (i.e., dyes and pigments) and non-colored or almost non-colored substance (i.e., color former or dye- or pigment-precursor) which develops to give a color under application of external energy (e.g., heating, pressing, light irradiation, etc.) or by contact with other components (i.e., developer). The light-sensitive material using the color image forming substance is described in Japanese Patent Provisional Publication No. 61(1986)-73145 (corresponding to U.S. Pat. No. 4,629,676 and European Patent Provisional Publication No. 0174634A2).

Examples of the dyes and pigments (i.e., colored substances) employable in the invention include commercially available ones, as well as various known compounds described in the technical publications, e.g., Yuki Gosei Kagaku Kyokai (ed.), Handbook of Dyes (in Japanese, 1970) and Nippon Ganryo Gijutsu Kyokai (ed.), New Handbook of Pigments (in Japanese, 1977). These dyes and pigments can be used in the form of a solution or a dispersion.

Examples of the substances which develop to give a color by certain energy includes thermochromic compounds, piezochromic compounds, photochromic compounds and leuco compounds derived from triarylmethane dyes, quinone dyes, indigoid dyes, azine dyes, etc. These compounds are capable of developing a color by heating, application of pressure, light-irradiation or air-oxidation.

Examples of the substances which develop to give a color in contact with other components include various compounds capable of developing a color through some reaction between two or more components, such as acid-base reaction, oxidation-reduction reaction, coupling reaction, chelating reaction, and the like. Examples of such color formation systems are described in Hiroyuki Moriga, "Introduction of Chemistry of Speciality Paper" (in Japanese, 1975), 29–58 (pressure-sensitive copying paper), 87–95 (azo-graphy), 118–120 (heat-sensitive color formation by a chemical change) or in MSS. of the seminer promoted by the Society of Kinki Chemical Industry, "The Newest Chemistry of Coloring Matter — Attractive Application and New Development as a Functional Coloring Matter", 26–32 (June, 19, 1980). Examples of the color formation systems specifically include a color formation system used in pressure-sensitive papers, etc., comprising a color former having a partial structure of lactone, lactam, spiropyran, etc., and an acidic substance (developer), e.g., acid clay, phenol, etc.; a system utilizing azo-coupling reaction between an aromatic a diazonium salt, diazotate or diazosulfonate and naphthol, aniline, active methylene, etc.; a system utilizing a chelating reaction, such as a reaction between hexamethylenetetramine and a ferric ion and gallic acid, or a reaction between a phenolphthalein-complexon and an alkaline earth metal ion; a system utilizing oxidation-reduction reaction, such as a reaction between ferric stearate and pyrogallol, or a reaction between silver behenate and 4-methoxy-1-naphthol, etc.

In the case that the color image forming substance comprising two components (e.g., a color former and a developer), one component and the polymerizable compound are contained in the microcapsule, and the other component is arranged outside of the microcapsule in the light-sensitive layer, a color image can be formed on the light-sensitive layer.

The color image forming substance in the light-sensitive material is preferably used in an amount of from 0.5 to 50 parts by weight, and more preferably from 2 to 30 parts by weight, per 100 parts by weight of the polymerizable compound. In the case that the developer is used, it is preferably used in an amount of from about 0.3 to about 80 parts by weight per one part by weight of the color former.

There is no specific limitation with respect to the sensitizing dyes, and known sensitizing dyes used in the conventional art of photography may be employed in the light-sensitive material. Examples of the sensitizing dyes include methine dyes, cyanine dyes, merocyanine dyes, complex cyanine dyes, complex merocyanine dyes, holopolar cyanine dyes, hemicyanine dyes, styryl dyes, and hemioxonol dyes. These sensitizing dyes can be used singly or in combination. Combinations of sensitizing dyes are often used for the purpose of supersensitization. In addition to the sensitizing dyes, a substance which does not per se exhibit spectral sensitization effect or does not substantially absorb visible light but shows supersensitizing activity can be used. The amount of the sensitizing dye to be added generally ranges from about $10^{-8}$ to about $10^{-2}$ mol per 1 mol of silver halide. The sensitizing dye is preferably added during the stage of the preparation of the silver halide emulsion (simultaneously with or after the grain formation).

When the heat development is employed in the use of the light-sensitive material, an organic silver salt is preferably contained in the light-sensitive material. It can be assumed that the organic silver salt takes part in a redox reaction using a silver halide latent image as a catalyst when heated to a temperature of 80° C. or higher. In such case, the silver halide and the organic silver salt preferably are located in contact with each other or close together. Examples of organic compounds employable for forming such organic silver salt include aliphatic or aromatic carboxylic acids, thiocarbonyl group-containing compounds having a mercapto group or an α-hydrogen atom, imino group-containing compounds, and the like. Among them, benzotriazoles are most preferable. The organic silver salt is preferably used in an amount of from 0.01 to 10 mol., and preferably from 0.01 to 1 mol., per 1 mol. of the light-sensitive silver halide. Instead of the organic silver salt, an organic compound (e.g., benzotriazole) which can form an organic silver salt in combination with an inoganic silver salt can be added to the light-sensitive layer to obtain the same effect.

Various image formation accelerators are employable in the light-sensitive material. The image formation accelerators have a function to accelerate the oxidation-reduction reaction between a silver halide (and/or an organic silver salt) and a reducing agent, a function to accelerate emigration of an image forming substance from a light-sensitive layer to an image-receiving material or an image-receiving layer, or a similar function. The image formation accelerators can be classified into oils, surface active agents, compounds functioning as an antifogging agent and/or a development accelerator, antioxidants and the like. These groups, however, generally have certain combined functions, i.e., two or more of the above-mentioned effects. Thus, the above classification is for the sake of convenience, and one compound often has a plurality of functions combined.

Various examples of these image formation accelerators are shown below.

Examples of the oils employable in the invention include high-boiling organic solvents which are used as solvents in emulsifying and dispersing hydrophobic compounds.

Examples of the surface active agents employable in the invention include pyridinium salts, ammonium salts and phosphonium salts as described in Japanese Patent Provisional Publication No. 59(1984)-74547; polyalkylene oxides as described in Japanese Patent Provisional Publication No. 59(1984)-57231.

The compounds functioning as an antifogging agent and/or a development accelerator are used to give a clear image having a high maximum density and a low minimum density (an image having high contrast). Examples of the compounds include a 5- or 6-membered nitrogen containing heterocyclic compound (e.g., a cyclic amide compound), a thiourea derivative, a thioether compound, a polyethylene glycol derivative, a thiol derivative, an acetylene compound and a sulfonamide derivative.

The antioxidants can be used to eliminate the influence of the oxygen which has an effect of inhibiting polymerization in the development process. Example of the antioxidants is a compound having two or more mercapto groups.

The thermal polymerization initiators employable in the light-sensitive material preferably are compounds that are decomposed under heating to generate a polymerization initiating species, particularly a radical, and those commonly employed as initiators of radical polymerization. The thermal polymerization initiators are described in "Addition Polymerization and Ring Opening Polymerization", 6–18, edited by the Editorial Committee of High Polymer Experimental Study of the High Polymer Institute, published by Kyoritsu Shuppan (1983). Examples of the thermal polymerization initiators include azo compounds, e.g., azobisisobutyronitrile, 1,1'-azobis(1-cyclohexanecarbonitrile), dimethyl 2,2'-azobisisobutyrate, 2,2'-azobis(2-methylbutyronitrile), and azobisdimethylvaleronitrile; organic peroxides, e.g., benzoyl peroxide, di-tert-butyl peroxide, dicumyl peroxide, tert-butyl hydroperoxide, and cumene hydroperoxide; inorganic peroxides, e.g., hydrogen peroxide, potassium persulfate, and ammonium persulfate; and sodium p-toluenesulfinate. The thermal polymerization initiators are preferably used in an amount of from 0.1 to 120% by weight, and more preferably from 1 to 10% by weight, based on amount of the polymerizable compound. In a system in which the polymerizable compound within the area where the latent image has not been formed is polymerized, the thermal polymerization initiators are preferably incorporated into the light-sensitive layer. The light-sensitive material employing the thermal polymerization initiators is described in Japanese Patent Provisional Publication No. 61(1986)-260241.

The development stopping agents employable in the light-sensitive material are compounds that neutralize a base or react with a base to reduce the base concentration in the layer to thereby stop development, or compounds that mutually react with silver or a silver salt to suppress development. More specifically, examples of the development stopping agents include acid precursors capable of releasing acids upon heating electrophilic compounds capable of undergoing substitution reaction with a coexisting base upon heating, nitrogen-containing heterocyclic compounds, mercapto compounds, and the like. Examples of the acid precursors include oxide esters described in Japanese Patent Provisional Publication Nos. 60(1985)-108837 and 60(1985)-192939 and compounds which release acids through Lossen rearrangement described in Japanese Patent Provisional Publication No. 60(1985)-230133. Examples of the electrophilic compounds which induce substitution reaction with bases upon heating are described in Japanese Patent Provisional Publication No. 60(1985)-230134.

The antismudging agents employable in the light-sensitive material preferably are particles which are solid at ambient temperatures. Examples of the antismudging agents include starch particles described in U.K. Pat. No. 1,232,347; polymer particles described in U.S. Pat. No. 3,625,736; microcapsule particles containing no color former described in U.K. Pat. No. 1,235,991; and cellulose particles, and inorganic particles, such as particles of talc, kaolin, bentonite, agalmatolite, zinc oxide, titanium dioxide or aluminum oxide described in U.S. Pat. No. 2,711,375. Such particles preferably have a mean size of 3 to 50 μm, more preferably 5 to 40 μm. When the microcapsule is employed in the light-sensitive material, the size of said particle is preferably larger than that of the microcapsule.

Binders employable in the light-sensitive material preferably are transparent or semi-transparent hydrophilic binders. Examples of the binders include natural substances, such as gelatin, gelatin derivatives, cellulose derivatives, starch, and gum arabic; and synthetic polymeric substances, such as water-soluble polyvinyl compounds e.g., polyvinyl alcohol, polyvinylpyrrolidone, and acrylamide polymers. In addition to the synthetic polymeric substances, vinyl compounds dispersed in the form of latex, which are particularly effective to increase dimensional stability of photographic materials, can be also used. These binders can be used singly or in combination. The light-sensitive material employing a binder is described in Japanese Patent Provisional Publication No. 61(1986)-69062 (corresponding to U.S. Pat. No. 4,629,676 and European Patent Provisional Publication No. 0174634A2).

The photo polymerization initiator can be contained in the light-sensitive layer to polymerize the unpolymerized polymerizable compound after the image-formation.

In the case that the solvent of the polymerizable compound is used, the solvent is preferably contained in a microcapsule which is different from the microcapsule containing the polymerizable compound.

Examples and usage of the other optional components which can be contained in the light-sensitive layer are also described in the above-mentioned publications and applications concerning the light-sensitive material, and in Research Disclosure Vol. 170, No. 17029, 9–15 (June 1978).

Examples of auxiliary layers which are optionally arranged on the light-sensitive material include an image-receiving layer, a heating layer, an antistatic layer, an anticurl layer, a release layer, a cover sheet or a protective layer.

Instead of the use of the image-receiving material, the image-receiving layer can be arranged on the light-sensitive material to produce the desired image on the image-receiving layer of the light-sensitive material. The image-receiving layer of the light-sensitive material can be constructed in the same manner as the layer of the image-receiving layer.

The light-sensitive material can be prepared, for instance, by the following process.

The light-sensitive material is usually prepared by dissolving, emulsifying or dispersing each of the components of the light-sensitive layer in an adequate medium to obtain coating solution, and then coating the obtained coating solution on a support.

The coating solution can be prepared by mixing liquid compositions each containing a component of the light-sensitive layer. Liquid composition containing two or more components may be also used in the preparation of the coating solution. Some components of the light-sensitive layer can be directly added to the coating solution or the liquid composition. Further, a secondary composition can be prepared by emulsifying the oily (or aqueous) composition in an aqueous (or oily) medium to obtain the coating solution.

The silver halide is preferably prepared in the form of a silver halide emulsion. Various processes for the preparation of the silver halide emulsion are known in the conventional technology for the preparation of photographic materials.

The silver halide emulsion can be prepared by the acid process, neutral process or ammonia process. In the stage for the preparation, a soluble silver salt and a halogen salt can be reacted in accordance with the single jet process, double jet process or a combination thereof. A reverse mixing method, in which grains are formed in the presence of excess silver ions, or a controlled double jet process, in which a pAg value is maintained constant, can be also employed. In order to accelerate grain growth, the concentrations or amounts or the silver salt and halogen salt to be added or the rate of their addition can be increased as described in Japanese Patent Provisional Publication Nos. 55(1980)-142329 and 55(1980) -158124, and U.S. Pat. No. 3,650,757, etc.

The silver halide emulsion may be of a surface latent image type that forms a latent image predominantly on the surface of silver halide grains, or of an inner latent image type that forms a latent image predominantly in the interior of the grains. A direct reversal emulsion comprising an inner latent image type emulsion and a nucleating agent may be employed. The inner latent image type emulsion suitable for this purpose is described in U.S. Pat. Nos. 2,592,250 and 3,761,276, Japanese Patent Publication No. 58(1983)-3534 and Japanese Patent Provisional Publication No. 57(1982)-136641, etc. The nucleating agent that is preferably used in combination with the inner latent image type emulsion is described in U.S. Pat. Nos. 3,227,552, 4,245,037, 4,255,511, 4,266,013 and 4,276,364, and West German Patent Provisional Publication (OLS) No. 2,635,316.

In the preparation of the silver halide emulsions, hydrophilic colloids are advantageously used as protective colloids. Examples of usable hydrophilic colloids include proteins, e.g., gelatin, gelatin derivatives, gelatin grafted with other polymers, albumin, and casein; cellulose derivatives, e.g., hydroxyethyl cellulose, carboxymethyl cellulose, cellulose sulfate, etc.; saccharide derivatives, e.g., sodium alginate and starch derivatives; and a wide variety of synthetic hydrophilic polymers, such as polyvinyl alcohol, polyvinyl alcohol partial acetal, poly-N-vinylpyrrolidone, polyacrylic acid, polymethacrylic acid, polyacrylamide, polyvinylimidazole, and polyvinylpyrazole, and copolymers comprising monomers constituting these homopolymers. Among them, gelatin is most preferred. Examples of employable gelatins include not only lime-processed gelatin, but also acid-processed gelatin and enzyme-processed gelatin. Hydrolysis products or enzymatic decomposition products of gelatin can also be used.

In the formation of silver halide grains in the silver halide emulsion, ammonia, an organic thioether derivative as described in Japanese Patent Publication No. 47(1972)-11386 or sulfur-containing compound as described in Japanese Patent Provisional Publication No. 53(1978)-144319 can be used as a silver halide solvent. Further, in the grain formation or physical ripening, a cadmium salt, a zinc salt, a lead salt, a thallium salt, or the like can be introduced into the reaction system. Furthermore, for the purpose of improving high or low intensity reciprocity law failure, a water-soluble iridium salt, e.g., iridium (III) or (IV) chloride, or ammonium hexachloroiridate, or a water-soluble rhodium salt, e.g., rhodium chloride can be used.

After the grain formation or physical ripening, soluble salts may be removed from the resulting emulsion by a known noodle washing method or a sedimentation method. The silver halide emulsion may be used in the primitive condition, but is usually subjected to chemical sensitization. Chemical sensitization can be carried out by the sulfur sensitization, reduction sensitization or noble metal sensitization, or a combination thereof that are known for emulsions for the preparation of the conventional light-sensitive materials.

When the sensitizing dyes are added to the silver halide emulsion, the sensitizing dye is preferably added during the preparation of the emulsion. When the organic silver salts are introduced in the light-sensitive microcapsule, the emulsion of the organic silver salts can be prepared in the same manner as in the preparation of the silver halide emulsion.

In preparation of the light-sensitive material, the polymerizable compounds are used as the medium for preparation of the liquid composition containing another component of the light-sensitive layer. For example, the silver halide, including the silver halide emulsion), the reducing agent, or the color image forming substance can be dissolved, emulsified or dispersed in the polymerizable compound to prepare the light-sensitive material. Especially, the triazene compound is preferably incorporated in the polymerizable compound. Further, the necessary components for preparation of a microcapsule, such as shell material can be incorporated into the polymerizable compound.

The light-sensitive composition which is the polymerizable compound containing the silver halide can be prepared using the silver halide emulsion. The light-sensitive composition can be also prepared using silver halide powders which can be prepared by lyophilization. These light-sensitive composition can be obtained by stirring the polymerizable compound and the silver halide using a homogenizer, a blender, a mixer or other conventional stirring device.

Polymers having a principal chain consisting essentially of a hydrocarbon chain substituted in part with hydrophilic groups which contain, in their terminal groups, -OH or nitrogen having a lone electron-pair are preferably introduced into the polymerizable compound prior to the preparation of the light-sensitive composition. The polymer has a function of dispersing silver halide or other component in the polymerizable compound very uniformly as well as a function of keeping thus dispered state. Further, the polymer has another function of gathering silver halide along the interface between the polymerizable compound (i.e., light-sensitive composition) and the aqueous medium in preparation of the microcapsule. Therefore, using this polymer, silver halide can be easily introduced into the shell material of the microcapsule.

The polymerizable compound (including the light-sensitive composition) are preferably emulsified in an aqueous medium to prepare the coating solution. The necessary components for preparation of the microcapsule, such as shell material can be incorporated into the emulsion. Further, other components such as the reducing agent can be added to the emulsion.

The emulsion of the polymerizable compound can be processed for forming shell of the microcapsule. Examples of the process for the preparation of the microcapsules include a process utilizing coacervation of hydrophilic wall-forming materials as described in U.S. Pat. Nos. 2,800,457 and 2,800,458; an interfacial polymerization process as described in U.S. Pat. No. 3,287,154, U.K. Patent No. 990,443 and Japanese Patent Publication Nos. 38(1963)-19574, 42(1967)--446 and 42(1967)-771; a process utilizing precipitation of polymers as described in U.S. Pat. Nos. 3,418,250 and 3,660,304; a process of using isocyanate-polyol wall materials as described in U.S. Pat. No. 3,796,669; a process of using isocyanate wall materials as described in U.S. Pat. No. 3,914,511; a process of using urea-formaldehyde or urea-formaldehyde-resorcinol wall-forming materials as described in U.S. Pat. Nos. 4,001,140, 4,087,376 and 4,089,802; a process of using melamine-formaldehyde resins hydroxypropyl cellulose or like wall-forming materials as described in U.S. Pat. No. 4,025,455; an in situ process utilizing polymerization of monomers as described in U.K. Patent No. 867,797 and U.S. Pat. No. 4,001,140; an electrolytic dispersion and cooling process as described in U.K. Pat. Nos. 952,807 and 965,074; a spray-drying process as described in U.S. Pat. No. 3,111,407 and U.K. Pat. 930,422; and the like. It is preferable, though not limitative, that the microcapsule is prepared by emulsifying core materials containing the polymerizable compound and forming a polymeric membrane (i.e., shell) over the core materials.

When the emulsion of the polymerizable compound (including the dispersion of the microcapsule) has been prepared by using the light-sensitive composition, the emulsion can be used as the coating solution of the light-sensitive material. The coating solution can be also prepared by mixing the emulsion of the polymerizable compound and the silver halide emulsion. The other components can be added to the coating solution in a similar manner as the emulsion of the polymerizable compound.

There is no specific limitation with respect to the addition of the base precursor, the catalyst, the ligand or the hot-melt solvent in the preparation of the light-sensitive material. In the case that the catalyst is separated from the base precursor and/or the ligand in the light-sensitive layer, the separating means such as microcapsules can be arranged in the light-sensitive layer as mentioned before.

A light-sensitive material can be prepared by coating and drying the above-prepared coating solution on a support in the conventional manner.

Use of the light-sensitive material is described below.

In the use of the light-sensitive material, a development process is conducted simultaneously with or after an imagewise exposure.

Various exposure means can be employed in the imagewise exposure, and in general, the latent image on the silver halide is obtained by imagewise exposure to radiation including visible light. The type of light source and exposure can be selected depending on the light-sensitive wavelengths determined by spectral sensitization or sensitivity of silver halide. Original image can be either monochromatic image or color image.

Development of the light-sensitive material can be conducted simultaneously with or after the imagewise exposure. The development can be conducted using a developing solution in the same manner as the image forming method described in Japanese Patent Publication No. 45(1970)-11149. The light-sensitive material can use a neutral developing solution according to the present invention.

The image forming method described in Japanese Patent Provisional Publication No. 61(1986)-69062 which employs a heat development process has an advantage of simple procedures and short processing time because of the dry process. Thus, this method is preferred as the development process of the light-sensitive material.

Heating in the heat development process can be conducted in various known manners. The heating layer which is arranged on the light-sensitive material can be used as the heating means in the same manner as the light-sensitive material described in Japanese Patent Provisional Publication No. 61(1986)-294434. Further,- the light-sensitive material can be heated while suppressing supply of oxygen into the light-sensitive layer from outside. Heating temperatures for the development process usually ranges from 80° C. to 200° C., and preferably from 100° C. to 160° C. Various heating patterns are applicable. The heating time is usually not shorter than 1 second, preferably from 1 second to 5 minutes, and more preferably from 1 second to 1 minute.

During the above development process, a polymerizable compound within the area where a latent image of the silver halide has been formed or within the area where a latent image of the silver halide has not been formed is polymerized. In a general system, the polymerizable compound within the area where the latent image has been formed is polymerized. If a nature or amount of the reducing agent is controlled, the polymerizable compound within the area where the latent image has not been formed can be polymerized.

In the above development process, a polymer image can be formed on the light-sensitive layer. A pigment iamge can be also obtained by fixing pigments to the polymer image.

Further, a color image can be formed on the light-sensitive material in which the light-sensitive layer contains a color former and a developer, one of them is together with the polymerizable compound contained in a microcapsule, and the other is arranged outside of the microcapsule.

The image can be also formed on the image-receiving material. The image-receiving material is described hereinbelow. The image forming method employing the image-receiving material or the image-receiving layer is described in Japanese Patent Provisional Publication No. 61(1986)-278849.

Examples of the material employable as the support of the image-receiving material include baryta paper in addition to various examples which can be employed as the support of the following light-sensitive material. In the case that a porous material, such as paper is used as the support of the image-receiving material, the porous support preferably has such a surface characteristic that a filtered maximum waviness of not less than 4 μm is observed in not more than 20 positions among 100 positions which are determined at random on a filtered waviness curve obtained according to JIS-B-0610. Further, a transparent material can be employed as the support of the image-receiving material to obtain a transparent or a projected image.

The image-receiving material is usually prepared by providing the image-receiving layer on the support. The image-receiving layer can be constructed according to the color formation system. In the case that a polymer image is formed on the image-receiving material and that a dye or pigment is employed as the color image forming substance, the image-receiving material can be composed of a simple support.

For example, when a color formation system using a color former and developer is employed, the developer can be contained in the image-receiving layer. Further, the image-receiving layer can be composed of at least one layer containing a mordant. The mordant can be selected from the compound known in the art of the conventional photography according to the kind of the color image forming substance. If desired, the image-receiving layer can be composed of two or more layers containing two or more mordants different in the mordanting power form each other.

The image-receiving layer preferably contains a polymer as binder. The binder which may be employed in the above-mentioned light-receiving layer is also employable in the image-receiving layer. Further, a polymer having a transmission coefficient of oxygen of not more than $1.0\times10^{-11}$ $cm^3\cdot cm/cm^2\cdot sec\cdot cmHg$ can be used as the binder to protect the color of the image formed on the image-receiving material.

The image-receiving layer can contain a granulated thermoplastic compound to obtain a glossy image. Further, the image-receiving layer can contain a white pigment (e.g., titanium dioxide) to function as a white reflection layer. Furthermore, a photo polymerization initiator or a thermalpolymerization initiator can be contained in the image-receiving layer to polymerize the unpolymerized polymerizable compound.

The image-receiving layer can be composed of two or more layers according to the above-mentioned functions. The thickness of the image-receiving layer preferably ranges from 1 to 100 μm, more preferably from 1 to 20 μm.

A protective layer can be provided on the surface of the image-receiving layer.

After the development process, pressing the light-sensitive material on the image-receiving material to transfer the unpolymerized polymerizable compound to the image-receiving material, a polymer iamge can be obtained in the image-receiving material. The process for pressing can be carried out in various known manners.

In the case that the light-sensitive layer contains a color image forming substance, the color image forming substance is fixed by polymerization of the polymerizable compound. Then, pressing the light-sensitive material on the image-receiving material to transfer the color image forming substance in unfixed area, a color image can be produced on the image-receiving material.

The light-sensitive material can be used for monochromatic or color photography, printing, radiography, diagnosis (e.g., CRT photography of diagnostic device using ultrasonic wave), copy (e.g., computer-graphic hard copy), etc.

The present invention is further described by the following examples without limiting the invention.

COMPARISON EXAMPLE 1

A solution (solvent: butyl acetate/ethylene glycol monomethyl ether=50/50 volume ratio) of the following base precursor (3) in an amount of $5\times10^{-2}$ mole/l was mole/l was heated to 80° C., and change in hydrogen ion concentration (pH) with time was measured.

(Base precursor (3))

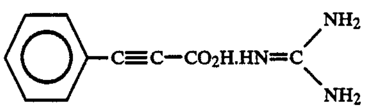

EXAMPLE 1

To 10 ml of the solution of the base precursor (3) used in Comparison Example 1 was added 0.1 equivalent (based on the amount of the base precursor) of the following catalyst (37). The mixture was then heated to 80° C. and pH change with time was measured.

(Catalyst (37))

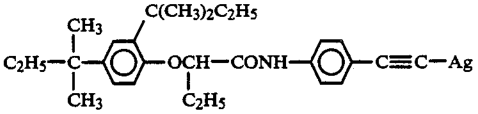

EXAMPLE 2

To 10 ml of the solution of the base precursor (3) used in Comparison Example 1 was added 0.01 equivalent (based on the amount of the base precursor) of the catalyst (37) used in Example 1. The mixture was then heated to 80° C. and pH change with time was measured.

The measurement results in Examples 1 & 2 and Comparison Example 1 are shown in FIG. 1.

In FIG. 1, the axis of abscissa represents the time (in minute) passed after the completion of heating the solution of the base precursor to 80° C., and the axis of ordinate represents the hydrogen ion concentration (pH) of the solution. The curve (—□—□—) shows the results of the measurement in Comparison Example 1, the curve (—Δ—Δ—) shows the results of the measurement in Example 1, and the curve (—o—o—) shows the results of the measurement in Example 2.

It is apparent from the results shown in FIG. 1 that the base precursor itself decomposes very slowly, but it is rapidly decomposed in the presence of the catalyst according to the present invention. The effect of the catalyst is remarkable even if only 0.01 equivalent of the catalyst based on the base precursor is used.

EXAMPLE 3

Application to Heat-Developable Diazotype Light-Sensitive Material

A diazonium salt composition composed of a mixture of the following components was coated on a base paper to give a layer having wet thickness of 100 μm.

| Diazonium salt composition | |
|---|---|
| 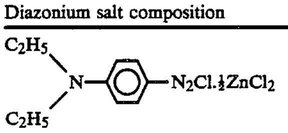 | 30 mg |
| Citric acid | 40 mg |
| Thiourea | 45 mg |
| (Base precursor (3)) | |
| 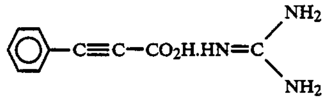 | 200 mg |
| 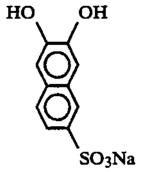 | 10 mg |
| Dispersion of fine particles of following Catalyst (30) | |
| 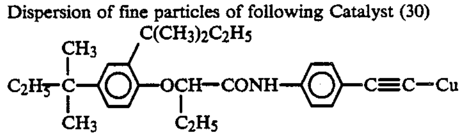 | 5 mg |
| Water | 5 ml |

After drying the obtained light-sensitive material, the material was exposed to light through a transparent text original in a conventional diazotype exposing machine. The exposed material was heated at 120° C. for 5 seconds. As a result, a blue-colored positive image having a high contrast (an optical density of 1.15) was obtained.

COMPARISON EXAMPLE 2

The procedure of Example 3 was repeated except that 100 mg of hexamethylenetetramine was used in place of a combination of the base precursor and the catalyst. As a result, an image having an optical density of 0.50 was obtained.

EXAMPLE 4

Preparation of Silver Halide Emulsion

In 3 l of water were dissolved 40 g of gelatin and 23.8 g of potassium bromide, and the resulting gelatin solution was kept at 50° C. To the gelatin solution, 200 ml of an aqueous solution containing 34 g of silver nitrate was added over a period of 10 minutes while stirring. To the solution, 100 ml of an aqueous solution containing 3.3 g of potassium iodide was added over a period of 2 minutes to obtain a silver bromoiodide emulsion. After the emulsion was adjusted to a pH for sedimentation, excess salts were removed, and the emulsion was adjusted to a pH of 6.0. The yield of the emulsion was 400 g.

Preparation of Light-Sensitive Composition

In 100 g of trimethylolpropane triacrylate were dissolved 0.40 g of the following copolymer and 6.00 g of Pargascript Red I-6-B (tradename of Chiba-Geigy).

(Copolymer)

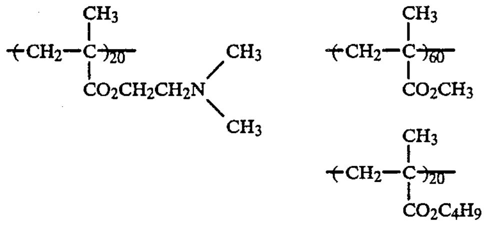

To 18.00 g of the resulting solution were added a solution in which 0.61 g of the following reducing agent (I) and 1.22 g of the following reducing agent (II) are dissolved in 1.80 g of methylene chloride.

(Reducing agent (I))

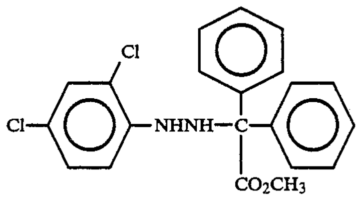

(Reducing agent (II))

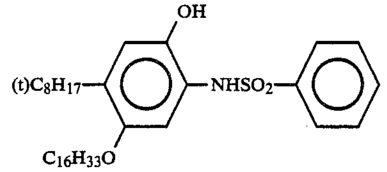

To the mixture was further added 4.06 g of the silver halide emulsion, and the mixture was stirred at 15,000 r.p.m. for 5 minutes to obtain a light-sensitive composition (average diameter of droplets: about 1 μm).

Preparation of Light-Sensitive Microcapsule

To 48.56 g of 2.89% aqueous solution of pectin was added 10.51 g of 18.6% aqueous solution of Isobam (tradename of Kuraray Co., Ltd.). After the solution was adjusted to a pH of 4.0 using 10% sulfuric acid, the light-sensitive composition was added to the resulting solution, and the mixture was stirred at 7,000 r.p.m. for 2 min. to emulsify the light-sensitive composition in the aqueous medium (average diameter of droplets: 8 μm).

To 72.5 g of the aqueous emulsion were added 8.32 g of 40% aqueous solution of urea, 2.82 g of 11.3% aqueous solution of resorcinol, 8.56 g of 37% aqueous solution of formaldehyde, and 2.74 g of 8.76% aqueous solution of ammonium sulfate in this order, and the mixture was heated at 60° C. for 2 hours while stirring. After the mixture was adjusted to a pH of 7.0 using 10% aqueous solution of sodium hydroxide, 3.62 g of 30.9% aqueous solution of sodium hydrogen sulfite was added to the mixture to obtain a dispersion containing light-sensitive microcapsules having a shell made of aminoaldehide resin.

Preparation of Dispersion of Base Precursor and Catalyst

In 10 g of 5% aqueous solution of polyvinyl alcohol were dispersed the following base precursor (3) and 1 g of copper (I) oxide (Catalyst (4)) to obtain a dispersion of the base precursor and the catalyst.

(Base precursor (3))

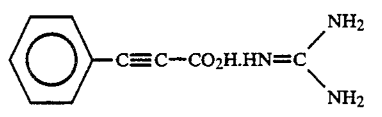

Preparation of Light-Sensitive Material

To 10.0 g of the light-sensitive microcapsule dispersion was added 0.03 g of the dispersion of the base precursor and the catalyst to prepare a coating solution.

The coating solution was uniformly coated on a polyethyleneterephthalate film using a coating rod of #30 to give a layer having a wet thickness of 53 μm and dried to obtain a light-sensitive material.

Preparation of Image-Receiving Material

To 125 g of water was added 11 g of 40% aqueous solution of sodium hexametaphosphate, and were further added 34 g of zinc 3,5-di-α-methylbenzylsalicylate and 82 g of 55% slurry of calcium carbonate, followed by coarsely dispersing in a mixer. The coarse dispersion was then finely dispersed in Dynomill dispersing device. To 200 g of the resulting dispersion were added 6 g of 50% latex of SBR (styrene-butadiene rubber) and 55 g of 8% aqueous solution of polyvinyl alcohol, and the resulting mixture was made uniform. The mixture was then uniformly coated on an art paper having a basis weight of 43 g/m$^2$ to give a layer having a wet thickness of 30 μm and dried to obtain an image-receiving material.

Evaluation of Light-Sensitive Material

The light-sensitive materials prepared in Example 5 was imagewise exposed to light using a halogen lamp at 1,000 lux for 2 second and then heated on a hot plate at 125° C. for 30 seconds. The exposed and heated light-sensitive material was then combined with the image-receiving material and passed through press rolls at a pressure of 350 kg/cm$^2$. As a resust, a clear magenta positive color image having reflection densities of 1.3 within the unexposed area and 0.1 within the exposed area was obtained on the image-receiving material, wherein the image was measured using a reflection densitometer.

EXAMPLE 5

Light-sensitive materials were prepared in the same manner as in Example 4 except that each of the catalysts set forth in Table 1 was respectively used in place of 1 g of the catalyst (4). Each of the light-sensitive materials was evaluated in the same manner as in Example 4. As a result, a clear image similar to Example 4 was obtained.

TABLE 1

| | Catalyst | Amount |
|---|---|---|
| (C-5) | Copper (II) oxide | 1 g |
| (C-27) | Copper (I) phenylacetylene | 1 g |
| (C-38) | Silver (I) phenylacetylene | 5 g |
| (C-24) | Silver (I) benzotriazole | 5 g |
| (C-2) | Metallic copper powder | 2 g |
| (C-11) | Copper (I) chloride | 1 g |
| (C-39) | Catalyst (39) below | 1 g |
| (C-25) | Acetylacetonatocopper (II) | 1 g |

(Catalyst (39))

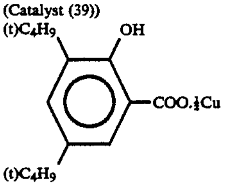

COMPARISON EXAMPLE 3

A light-sensitive material was prepared in the same manner as in Example 4 except that 1 g of the catalyst (4) was not used. The light-sensitive material was evaluated in the same manner as in Example 4. The obtained image was not clear. In order to obtain a clear image (having reflection densities of 1.3 within the unexposed area and 0.1 within the exposed area), the heating time should be prolonged from 30 seconds in Example 4 to 100 seconds.

EXAMPLE 6

A light-sensitive material was prepared in the same manner as in Example 4 except that 0.1 g of phenidone (reducing agent (III)) and 0.2 g of 1,1'-azobis(1-cyclohexanecarbonitrile) (thermal polymerization initiator) was used in place of 0.61 g of the reducing agent (I) and 1.22 g of the reducing agent (II). The light-sensitive material was evaluated in the same manner as in Example 4. As a resust, a clear magenta negative color image having reflection density values of 1.3 within the exposed area and 0.1 within the unexposed area was obtained on the image-receiving material, wherein the image was measured using a reflection densitometer.

EXAMPLE 7

Preparation of Dispersion of Catalyst

In 4.5 g of chloroform was dissolved 0.1 g of the following catalyst (40).

(Catalyst (40))

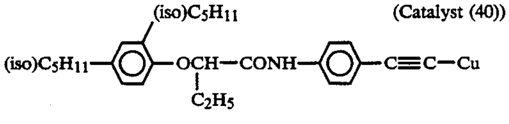

To 15 g of 5% aqueous solution of polyvinyl alcohol was added the resulting solution of the catalyst, and the mixture was emulsified in a homogenizer. The emulsion was further stirred at 40° C. for 2 hours to obtain a dispersion of the catalyst.

Preparation of Light-Sensitive Material

To 10.0 g of the light-sensitive microcapsule dispersion used in Example 4 were added 0.6 g of the base precursor (3) used in Example 4, 2.5 g of the dispersion of the catalyst and 6.0 g of water to prepare a coating solution.

The coating solution was uniformly coated on a polyethyleneterephthalate film using a coating rod of #40 to give a layer having a wet thickness of 70μm and dried to obtain a light-sensitive material.

EXAMPLE 8

Preparation of Dispersion of Microcapsules Containing Catalyst

In 4.5 g of chloroform was dissolved 0.1 g of the catalyst (40) used in Example 6. To the solution was added 1.5 g of an isocyanate compound (Takenate D-110N; tradename of Takeda Chemical Industries, Ltd.). To 15 g of 5% aqueous solution of polyvinyl alcohol was added the resulting solution of the catalyst, and the mixture was emulsified in a homogenizer. The emulsion was further stirred at 40° C. for 2 hours to obtain a dispersion of polyurea microcapsules containing the catalyst.

Preparation of Light-Sensitive Material

To 10.0 g of the light-sensitive microcapsule dispersion used in Example 4 were added 0.6 g of the base precursor (3) used in Example 4, 2.5 g of the dispersion of microcapsules containing the catalyst and 6.0 g of water to prepare a coating solution.

The coating solution was uniformly coated on a polyethyleneterephthalate film using a coating rod of #40 to give a layer having a wet thickness of 70 μm and dried to obtain a light-sensitive material.

EXAMPLE 9

Preparation of Particles Containing Catalyst

A mixture of 0.1 g of the catalyst (40) used in Example 6 and 3 g of the following hot-melt solvent (1) was heated at 100° C. to be fused. The mixture was stirred and then cooled to solidify. The solid was ground to obtain particles containing the catalyst.

(Hot-melt solvent (1))

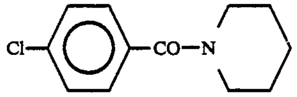

Preparation of Light-Sensitive Material

To 10.0 g of the light-sensitive microcapsule dispersion used in Example 4 were added 0.6 g of the base precursor (3) used in Example 4, 0.5 g of the particles containing the catalyst and 6.0 g of water to prepare a coating solution.

The coating solution was uniformly coated on a polyethyleneterephthalate film using a coating rod of #40 to give a layer having a wet thickness of 70 μm and dried to obtain a light-sensitive material.

EXAMPLE 10

Preparation Of Light-Sensitive Material

To 10.0 g of the light-sensitive microcapsule dispersion used in Example 4 were added 0.6 g of the base precursor (3) used in Example 4, 2.5 g of the dispersion of microcapsules containing the catalyst used in Example 8, 2.5 g of sorbitol (hot-melt solvent), 2.5 g of 5% aqueous solution of polyvinyl alcohol and 6.0 g of water to prepare a coating solution.

The coating solution was uniformly coated on a polyethyleneterephthalate film using a coating rod of #40 to give a layer having a wet thickness of 70 μm and dried to obtain a light-sensitive material.

EXAMPLE 11

Preparation Of Light-Sensitive Material

To 10.0 g of the light-sensitive microcapsule dispersion used in Example 4 were added 0.6 g of the base precursor (3) used in Example 4, 2.5 g of the dispersion of microcapsules containing the catalyst used in Example 8, 1.0 g of 1% ethanol solution of salicylaldoxime (ligand), 2.5 g of sorbitol (hot-melt solvent), 2.5 g of 5% aqueous solution of polyvinyl alcohol and 6.0 g of water to prepare a coating solution.

The coating solution was uniformly coated on a polyethyleneterephthalate film using a coating rod of #40 to give a layer having a wet thickness of 70 μm and dried to obtain a light-sensitive material.

EXAMPLE 12

Preparation of Light-Sensitive Material

A light-sensitive material was prepared in the same manner as in the same manner as in Example 11, except that 1.0 g of 1% ethanol solution of 8-hydroxyquinoline (ligand) was used in place of 1.0 g of 1% ethanol solution of salicylaldoxime.

EXAMPLE 13

PREPARATION OF LIGHT-SENSITIVE MATERIAL

A light-sensitive material was prepared in the same manner as in the same manner as in Example 11, except as in the same manner as in Example 11, except that 0.2 mole (based on 1 mole of the catalyst) of disodium ethylenediaminetetraacetate (ligand) was used in place of 1.0 g of 1% ethanol solution of salicylaldoxime.

EXAMPLE 14

PREPARATION OF LIGHT-SENSITIVE MATERIAL

A light-sensitive material was prepared in the same manner as in the same manner as in Example 11, except that 2.5 g of mannitol (hot-melt solvent) was used in place of 2.5 g of sorbitol.

EXAMPLE 15

PREPARATION OF LIGHT-SENSITIVE MATERIAL

A light-sensitive material was prepared in the same manner as in the same manner as in Example 11, except that 2.5 g of sorbitol (hot-melt solvent) was not used.

EVALUATION OF LIGHT-SENSITIVE MATERIAL

Each of the light-sensitive materials prepared in Examples 7 to 15 was evaluated in the same manner as in Example 4. As a result, a clear magenta positive image was obtained on each of the image-receiving materials. All of the obtained images were similar to each other.

Further, each of the light-sensitive materials was preserved at 50° C. in a thermostat in a dark place, and then evaluated as mentioned above to determine the preservability of each of the materials. The preservability was measured as the term required in which the increase of the fog density in the image became 0.1.

The results are set forth in Table 2.

TABLE 2

| Light-sensitive Material | Separating Means | Free Ligand | Hot melt Solvent | Preservability at 50° C. |
|---|---|---|---|---|
| Example 7 | — | — | — | 2 days |
| Example 8 | Capsule | — | — | 3 days |
| Example 9 | Particle | — | (S-1) | 3 days |
| Example 10 | Capsule | — | Sorbitol | 3 days |
| Example 11 | Capsule | Salicylaldoxim | Sorbitol | 10 days |
| Example 12 | Capsule | 8-hydroxyquinoline | Sorbitol | 10 days |
| Example 13 | Capsule | EDTA | Sorbitol | 10 days |
| Example 14 | Capsule | Salicylaldoxim | Mannitol | 10 days |
| Example 15 | Capsule | Salicylaldoxim | — | 5 days |

We claim:

1. In a process for formation of a base from a base precursor having the following formula (I) or (II):

$$(R^1—C{\equiv}C—CO_2H)_x.B \quad (I)$$

$$R^2(—C{\equiv}C—CO_2H)_2.B_y \quad (II)$$

wherein $R^1$ is a monovalent group selected from the group consisting of hydrogen, an alkyl group, a cycloalkyl group, an alkenyl group, an alkynyl group, an aryl group, a heterocyclic group, an aralkyl group, an acyl group, an alkoxycarbonyl group, carbamoyl, $—CO_2M$ (M is an alkali metal), and $—CO_2HB$, each of which may have one or more substituent groups; $R^2$ is a divalent group selected from the group consisting of an alkylene group, an arylene group and a divalent heterocyclic group, each of which may have one or more substituent groups; B is an organic base; x is 1 when B is a monoacidic base, and x is 2 when B is a diacidic base; and y is 2 when B is a monoacidic base, and y is 1 when B is a diacidic base, the improvement wherein the process comprises decomposing the base precursor in the presence of a catalyst selected from the group consisting of copper and a copper compound at a temperature of not lower than 50° C., said catalyst being used in an amount of 0.001 to 1 mole per mole of the base precursor.

2. The process as claimed in claim 1, wherein the catalyst is a copper compound selected from the group consisting of an oxide, a sulfide, a halide, a salt of a carboxylic acid and a substituted acetylide.

3. The process as claimed in claim 1, wherein the catalyst is a copper compound having the following formula (III):

$$M'_mX_nL_l \quad (III)$$

wherein M' is a cation derived from copper; X is an anion; L is a ligand; m is 1 or 2; n is 0, 1 or 2; and l is an integer from 0 to 6.

4. The process as claimed in claim 1, wherein the catalyst is a substituted cuprous acetylide or cuprous chloride.

* * * * *